United States Patent [19]

Rousseaux et al.

[11] Patent Number: 5,374,416

[45] Date of Patent: Dec. 20, 1994

[54] NITROGENOUS MACROCYCLIC LIGANDS, POLYMETALLIC COMPLEXES AND DIAGNOSTIC AND THERAPEUTIC COMPOSITION

[75] Inventors: Olivier Rousseaux, Aulnay Sous Bois; Michel Schaefer, Lagny; Anne Bouillot, Boulogne-Billancourt; Dominique Meyer, Saint Maur Des Fosses, all of France

[73] Assignee: Guerbet S.A., Villepinte, France

[21] Appl. No.: 924,016

[22] PCT Filed: Jan. 22, 1992

[86] PCT No.: PCT/FR92/00057

§ 371 Date: Nov. 17, 1992

§ 102(e) Date: Nov. 17, 1992

[87] PCT Pub. No.: WO92/12978

PCT Pub. Date: Aug. 6, 1992

[30] Foreign Application Priority Data

Jan. 24, 1991 [FR] France ................... 9100811

[51] Int. Cl.$^5$ ............... A61K 49/00; A61K 49/04; C07D 403/04; C07D 403/06
[52] U.S. Cl. ..................... 424/2; 424/1.65; 424/4; 424/7.1; 424/9; 436/173; 534/10; 534/11; 534/13; 534/14; 534/15; 534/16; 540/465; 540/474; 128/653.4
[58] Field of Search ............ 540/465, 474; 424/1.1, 424/2, 4, 7.1, 9, 1.65; 534/10, 11, 13, 14, 15, 16

[56] References Cited

U.S. PATENT DOCUMENTS 4,174,319 11/1979 Kobuke ................... 540/474

FOREIGN PATENT DOCUMENTS 0299795 1/1989 European Pat. Off. .
305320 3/1989 European Pat. Off. ......... 540/474
0374929 6/1990 European Pat. Off. .

OTHER PUBLICATIONS

March, *Advanced Organic Chemistry*, 2d ed., (1977), pp. 326, 377–378.

Kodama et al., *Inorganic Chemistry*, vol. 30, No. 6, (1991), pp. 1270–1273.

Helps et al.: "General routes for the synthesis of mono, di and tri-N-substituted derivatives of cyclam", Tetrahedron, vol. 45, No. 1, Jan. 1989, pp. 219–226.

Cox et al.: "Synthesis of a kinetically stable yttrium–90 labelled macrocycle–Antibody conjugate" J. Chem Soc., Chemical Communications, No. 12, Jun. 1989, pp. 797–798.

*Primary Examiner*—Mukund J. Shah
*Assistant Examiner*—Philip I. Datlow
*Attorney, Agent, or Firm*—Wegner, Cantor, Mueller & Player

[57] ABSTRACT

The invention relates to ligands of formula

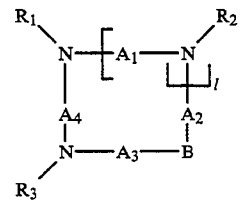

in which B represents an

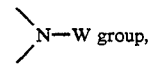

W representing the

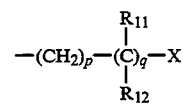

or (Abstract continued on next page.)

-continued

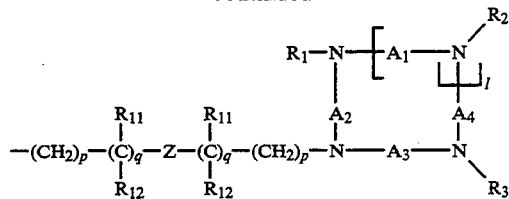

group, in which groups X and Z represent a heterocycle.

The invention also relates to the monometallic or polymetallic complexes formed by these ligands with metal ions chosen from lanthanide ions, transition metal ions, barium, bismuth, lead and the radioisotopes $^{99m}Tc$, $^{111}In$, $^{90}Y$, $^{64}Cu$ and $^{169}Yb$, as well as the physiologically acceptable salts of these complexes.

The salts of these complexes may be used as diagnostic or therapeutic agents in nuclear magnetic resonance imaging and X-ray radiology, as in-vivo chemical shift agents and in nuclear medicine.

No figure

19 Claims, No Drawings

NITROGENOUS MACROCYCLIC LIGANDS, POLYMETALLIC COMPLEXES AND DIAGNOSTIC AND THERAPEUTIC COMPOSITION

The present invention relates to new nitrogenous cyclic ligands and metal complexes formed by these ligands and to the diagnostic and therapeutic applications of these complexes, in particular in nuclear magnetic resonance imaging, in X-ray radiology, as in-vivo chemical shift agents and in nuclear medicine.

The invention also relates to a process for the preparation of these ligands.

The invention thus relates to ligands of formula I

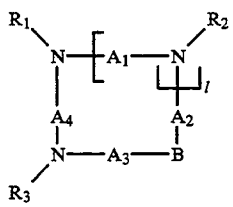

in which $A_1$, $A_2$, $A_3$ and $A_4$, which may be identical or different, independently of one another represent a group:

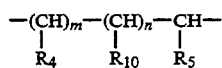

m and n being identical or different integers such that the sum of m and n is between 1 and 5, $R_4$ and $R_5$, which may be identical or different, represent a hydrogen atom, a straight-chain or branched $C_1$–$C_6$ alkyl group, a straight-chain or branched $C_1$–$C_6$ hydroxyalkyl or polyhydroxyalkyl group, a functional group enabling the macrocycle of formula I to be attached to a macromolecule, a straight-chain or branched $C_1$–$C_6$ alkoxy-$C_1$–$C_6$ alkyl group, a straight-chain or branched hydroxy-$C_1$–$C_6$-alkoxy-$C_1$–$C_6$ alkyl group or a straight-chain or branched polyhydroxy-$C_1$–$C_6$ alkoxy-$C_1$–$C_6$-alkyl group an aryl group or an aryl group substituted by one or more identical or different substituents chosen from a halogen atom, a hydroxyl group, a nitro group or a $C_1$–$C_6$ alkoxy and $C_1$–$C_6$ hydroxyalkyl, $C_1$–$C_6$ polyhydroxyalkyl, $C_1$–$C_6$ alkoxy and $C_1$–$C_6$ alkoxy-$C_1$–$C_6$-alkyl group, an aralkyl group or an aralkyl group substituted by one or more identical or different substituents chosen from a halogen atom, a hydroxyl group, a nitro group or a $C_1$–$C_6$ alkyl, $C_1$–$C_6$ hydroxyalkyl, $C_1$–$C_6$ polyhydroxyalkyl, $C_1$–$C_6$ alkoxy or $C_1$–$C_6$ alkoxy-$C_1$–$C_6$-alkyl group, the alkyl radical of the aralkyl group being $C_1$–$C_6$ and straight-chain or branched, $R_{10}$ represents the group $R_4$ or $R_5$, a hydroxyl group or a $C_1$–$C_5$ alkoxy group, $R_1$, $R_2$ and $R_3$, which may be identical or different, are chosen from a hydrogen atom and the

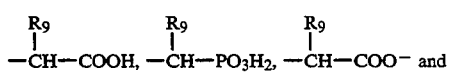

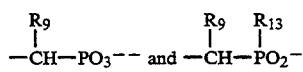

groups, $R_9$ representing a hydrogen atom, a straight-chain or branched $C_1$–$C_6$ alkyl group, a straight-chain or branched $C_1$–$C_6$ hydroxyalkyl group, a straight-chain or branched $C_1$–$C_6$ polyhydroxyalkyl group or a straight-chain or branched $C_1$–$C_6$ alkoxy-$C_1$–$C_6$-alkyl group and $R_{13}$ representing a straight-chain or branched $C_1$–$C_6$-hydroxyalkyl group, a straight-chain or branched $C_1$–$C_6$-hydroxyalkyl or-polyhydroxyalkyl group, a straight-chain or branched $C_1$–$C_6$ alkoxy-$C_1$–$C_6$ alkyl group or a straight-chain or branched $C_1$–$C_6$-hydroxyalkoxy- or -polyhydroxyalkoxy-$C_1$–$C_6$ group, B represents the group

W representing the group

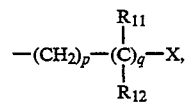

in which p and q are identical or different integers from 0 to 6, $R_{11}$ and $R_{12}$, which may be identical or different, have the same meaning as $R_{10}$ when p is other than 0 and have the same meaning as $R_4$ and $R_5$ when p is equal to 0 and X represents a group

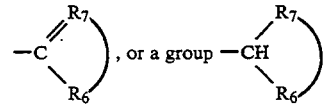

$R_6$ and $R_7$ forming, with the carbon atom to which they are attached, a heterocycle, optionally composed of 2 fused rings, containing up to 12 members, 1 to 4 of which are heteroatoms chosen from oxygen,

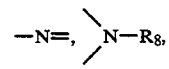

$R_8$ representing a hydrogen atom, a straight-chain or branched $C_1$–$C_6$ alkyl group, a straight-chain or branched $C_1$–$C_6$ hydroxyalkyl group, a straight-chain or branched $C_1$–$C_6$ polyhydroxyalkyl group or a straight-chain or branched $C_1$–$C_6$ alkoxy group, phosphorus and sulphur, the heterocycle being optionally substituted by one or more groups chosen from hydroxyl, mercapto, straight-chain or branched $C_1$–$C_6$ alkyl, straight-chain or branched $C_1$–$C_6$ hydroxyalkyl, straight-chain or branched $C_1$–$C_6$ polyhydroxyalkyl, straight-chain or branched $C_1$–$C_6$ alkoxy $C_1$–$C_6$ -alkyl, straight-chain or branched $C_1$–$C_6$ hydroxyalkoxy-$C_1$–$C_6$-alkyl and straight-chain or branched $C_1$–$C_6$ polyhydroxyalkoxy-$C_1$–$C_6$-alkyl groups, and a functional group enabling the heterocycle to be attached to a macromolecule, with the proviso that when p and q are equal to 0, $R_6$ and $R_7$ represent a —$CH_2$—, —CH= or

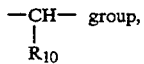 group, $R_{10}$ being as defined above; or W representing a group

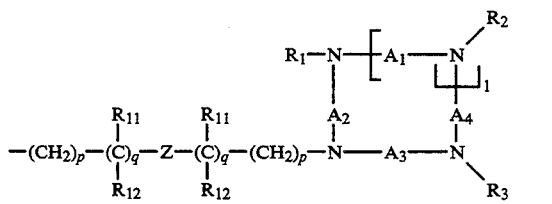

in which p, q, $R_1$, $R_2$, $R_3$, $R_{11}$, $R_{12}$, $A_1$, $A_2$, $A_3$ and $A_4$ are as defined above and Z represents a heterocycle, optionally formed from two fused rings, containing up to 12 members, 1 to 4 of which are heteroatoms chosen from oxygen, —N=,

$R_8$ being as defined above, phosphorus and sulphur, the heterocycle being optionally substituted by one or more groups chosen from hydroxyl, mercapto, straight-chain or branched $C_1$–$C_6$ alkyl, straight-chain or branched $C_1$–$C_6$-hydroxyalkyl or -polyhydroxyalkyl, straight-chain or branched $C_1$–$C_6$-alkoxy-$C_1$–$C_6$ alkyl and straight-chain or branched $C_1$–$C_6$-hydroxyalkoxy- or -polyhydroxyalkoxy-$C_1$–$C_6$-alkyl, and a functional group enabling the binding of a macromolecule; l represents an integer from 0 to 5; on condition that at least two of the groups $R_1$, $R_2$ and $R_3$ represent

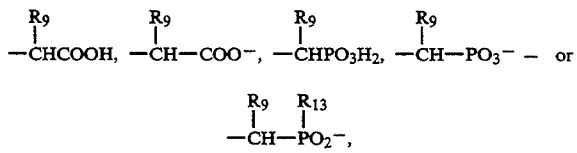

$R_9$ and $R_{13}$ being as defined above; it being understood that the groups $A_1$, $R_2$, $R_4$, $R_5$, $R_8$, $R_9$, $R_{10}$, $R_{11}$, $R_{12}$ and $R_{13}$ may differ from $A_1$, $R_2$, $R_4$, $R_5$, $R_8$, $R_9$, $R_{10}$, $R_{11}$, $R_{12}$ and $R_{13}$ respectively when l, m, n and q are other than 0, or when several of said groups are present, as well as the salts of these compounds formed with inorganic or organic bases, or basic amino acids.

Preferred compounds of formula I are those corresponding to the general formula II:

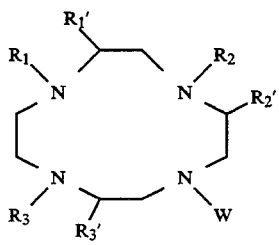

in which $R_1$, $R_2$, $R_3$ and W have the same meaning as above and $R'_1$, $R'_2$ and $R'_3$, which may be identical or different, represent the group $R_4$ or $R_5$.

Compounds of general formula II in which $R_1$, $R_2$ and $R_3$ represent the $CH_2$—COOH group are particularly preferred.

Amongst these compounds, further preferred compounds are the group of compounds of general formula III:

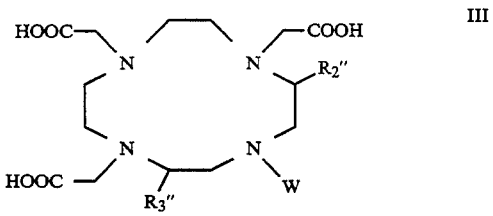

in which $R''_2$ and $R''_3$ are chosen from a hydrogen atom, a methyl group and an ethyl group, W being as defined above.

Amongst the preferred groups X, the following may be mentioned: thienyl, dihydrothienyl, tetrahydrothienyl, furyl, dihydrofuryl, tetrahydrofuryl, pyranyl, dihydropyranyl, tetrahydropyranyl, pyrrolyl, 2H-pyrrolyl, dihydropyrrolyl, tetrahydropyrrolyl, imidazolyl, pyrazolyl, pyridyl, 3-hydroxy-6-methyl-2-pyridyl, pyrazinyl, pyrimidinyl, pyridazinyl, thiazolyl, isothiazolyl, oxazolyl, isoxazolyl, furazanyl, pyrrolidinyl, Δ2-pyrrolinyl, imidazolidinyl, Δ2-imidazolinyl, pyrazolidinyl, Δ3-pyrazolinyl, piperidinyl, piperazinyl, morpholinyl, pyranyl, tetrahydropyranyl, tetrazoyl, dioxanyl and dioxolanyl groups, optionally substituted by one or more groups chosen from hydroxyl, mercapto, straight-chain or branched $C_1$–$C_6$ alkyl, straight-chain or branched $C_1$–$C_6$ hydroxyalkyl, straight-chain or branched $C_1$–$C_6$ polyhydroxyalkyl, straight-chain or branched $C_1$–$C_6$ alkoxy, straight-chain or branched $C_1$–$C_6$ alkoxy-$C_1$–$C_6$ alkyl , straight-chain or branched $C_1$–$C_6$ hydroxyalkoxy-$C_1$–$C_6$ alkyl and straight-chain or branched $C_1$–$C_6$ polyhydroxyalkoxy-$C_1$–$C_6$ alkyl.

The following groups are particularly preferred: pyrrolidinyl, imidazolyl, oxazolyl, pyrrolyl, pyridyl, pyranyl, tetrahydropyranyl, furyl, dihydrofuryl, tetrahydrofuryl, dioxanyl, oxazinyl, thienyl, morpholinyl, piperidinyl and dioxolanyl, in which groups the nitrogen atom is optionally substituted by a $C_1$–$C_6$ alkyl group, a straight-chain or branched $C_1$–$C_6$ hydroxyalkyl group, a straight-chain or branched $C_1$–$C_6$ polyhydroxyalkyl group or a straight-chain or branched $C_1$–$C_6$ alkoxy group, and the heterocycle is optionally substituted by one or more groups chosen from hydroxyl, mercapto, $C_1$–$C_6$ alkyl and $C_1$–$C_6$ hydroxyalkyl.

In addition, amongst the preferred groups X consisting of two fused rings, the following may be mentioned: benzofuryl, isobenzofuryl, chromenyl, indolizinyl, isoindolyl, indolyl, indazolyl, purinyl, quinolyl, phthalazinyl, quinazolinyl, pteridinyl, isochromanyl, indolinyl and isoindolinyl groups, optionally substituted by one or more groups chosen from hydroxyl, mercapto, straight-chain or branched $C_1$–$C_6$ alkyl, straight-chain or branched $C_1$–$C_6$ hydroxyalkyl, straight-chain or branched $C_1$–$C_6$ polyhydroxyalkyl, straight-chain or branched $C_1$–$C_6$ alkoxy, straight-chain or branched $C_1$–$C_6$ alkoxy-$C_1$–$C_6$ alkyl, straight-chain or branched $C_1$-$C_6$ hydroalkoxy-$C_1$-$C_6$- alkyl and straight-chain or branched $C_1$-$C_6$-polyhydroxyalkoxy -$C_1$-$C_6$ alkyl.

Amongst the preferred groups Z, the following groups may be mentioned: thiophenediyl, dihydrothiophenediyl, tetrahydrothiophenediyl, furandiyl, dihydrofurandiyl, tetrahydrofurandiyl, pyrandiyl, dihydropyrandiyl, tetrahydropyrandiyl, pyrrolediyl, 2H-pyrrolediyl, dihydropyrrolediyl, tetrahydropyrrolediyl, imidazolediyl, pyrazolediyl, pyridinediyl, 3-hydroxy-6-methyl-2-pyridinediyl, pyrazinediyl, pyrimidinediyl, pyridazinediyl, thiazolediyl, isothiazolediyl, oxazolediyl, isoxazolediyl, furazandiyl, pyrrolidinediyl, Δ2-pyrrolinediyl, imidazolinediyl, Δ2-imidazolinediyl, pyrazolidinediyl, Δ3-pyrazolinediyl, piperidinediyl, piperazinediyl, morpholinediyl, pyrandiyl, tetrahydropyrandiyl, tetrazolediyl, dioxanediyl, dioxolanediyl, benzofurandiyl, isobenzofurandiyl, chromenediyl, indolizinediyl, purinediyl, quinolinediyl, phthalazinediyl, quinazolinediyl, pteridinediyl, isochromandiyl, indolediyl, isoindolediyl, indazolediyl, indolinediyl and isoindolinediyl.

In general, the preferred heterocycles are those in which a heteroatom is placed in the β-position with respect to the nitrogen of the macrocycle.

Amongst the functional groups enabling a macromolecule to be attached to the macrocycle or to the heterocycle, the following groups may be mentioned in particular:

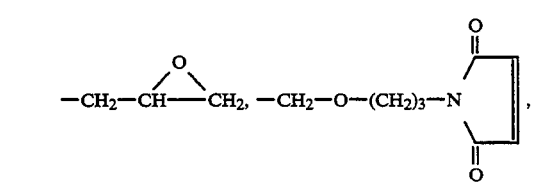

—CH$_2$—O—(CH$_2$)$_4$—SH,   —CH$_2$—O—(CH$_2$)$_3$—NHNH$_2$,

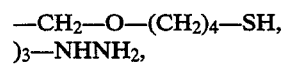

—CH$_2$—O—CH$_2$—CH$_2$—NH$_2$,

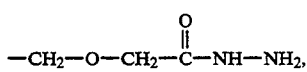

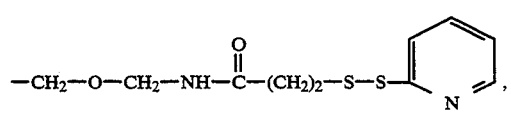

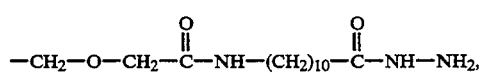

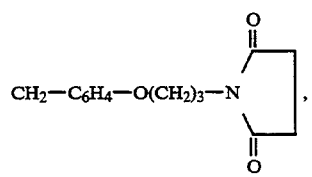

CH$_2$—C$_6$H$_4$—O(CH$_2$)$_5$CO$_2$CH$_2$C$_6$H$_5$,   —CH$_2$—C$_6$H$_4$—O—CH$_2$—CO$_2$—CH$_2$C$_6$H$_5$   —CH$_2$—C$_6$H$_4$—O(CH$_2$)$_5$CONHNH$_2$,

CH$_2$—C$_6$H$_4$—O(CH$_2$)$_4$—SH,   CH$_2$—C$_6$H$_4$—O(CH$_2$)$_3$NHNH$_2$,

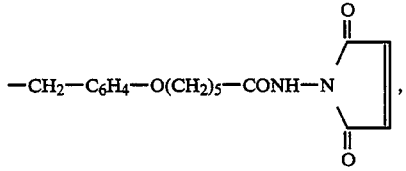

—CH$_2$—C$_6$H$_4$—O(CH$_2$)$_3$Br,   CH$_2$—C$_6$H$_4$—O(CH$_2$)$_5$CONHNH—(CH$_2$)$_3$—NHNH$_2$,   —CH$_2$—SH, CH$_2$—NHNH$_2$, —CH$_2$CONHNH$_2$, (CH$_2$)$_3$SH, —CH$_2$—C$_6$H$_4$—O—CH$_2$—COBr, —C$_6$H$_4$NHCOCH$_2$Br,

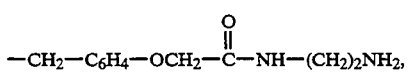

—CH$_2$—C$_6$H$_4$—NH$_2$, —C$_6$H$_4$—N$_2$, —C$_6$H$_4$NCS,

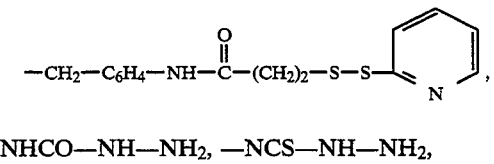

—NHCO—NH—NH$_2$, —NCS—NH—NH$_2$,

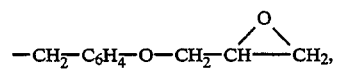

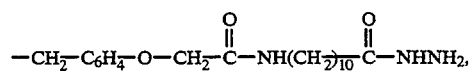

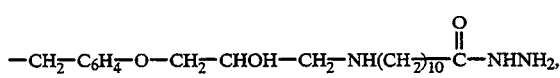

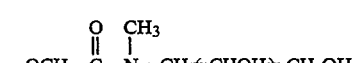

Amongst the compounds of formula I which are preferred, compounds which may be mentioned are those in which W represents the groups:

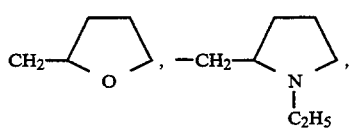

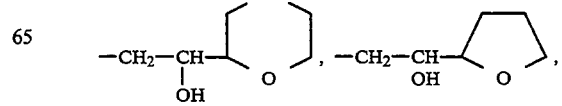

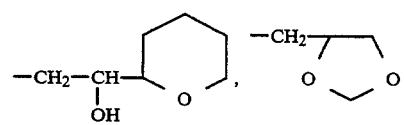
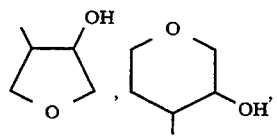
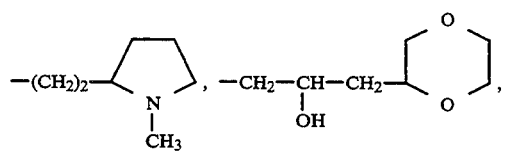
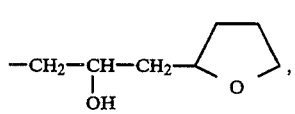
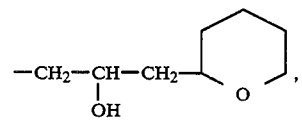
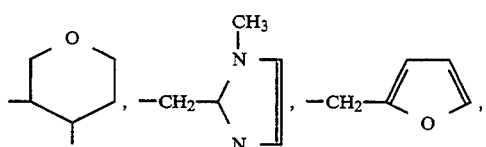
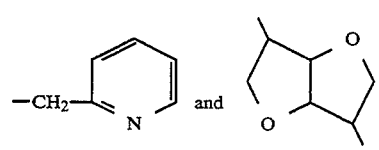
The following compounds of formula I are particularly preferred:
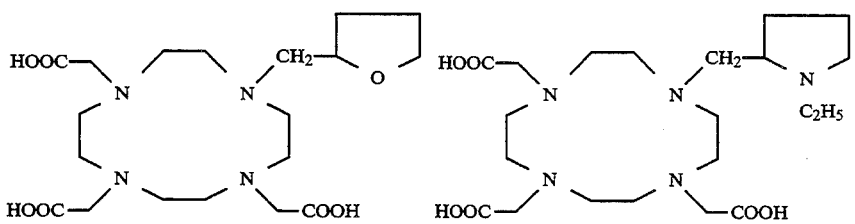
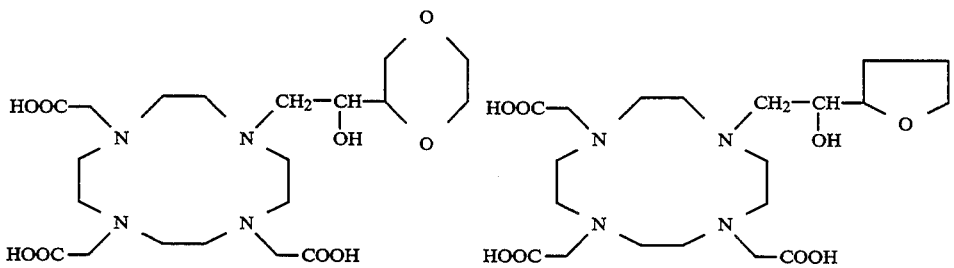
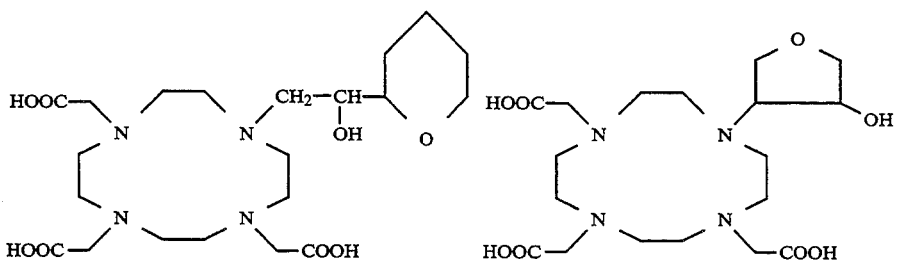
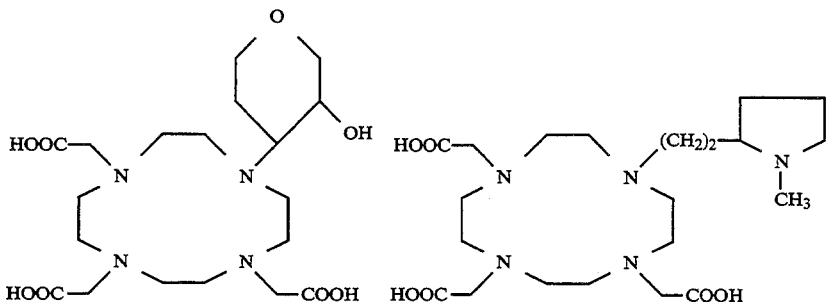

-continued
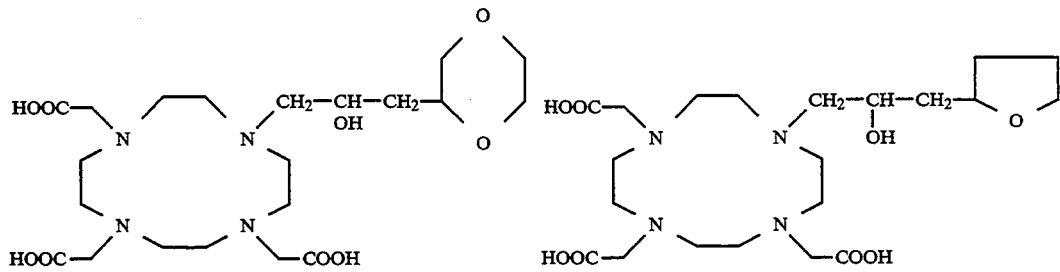
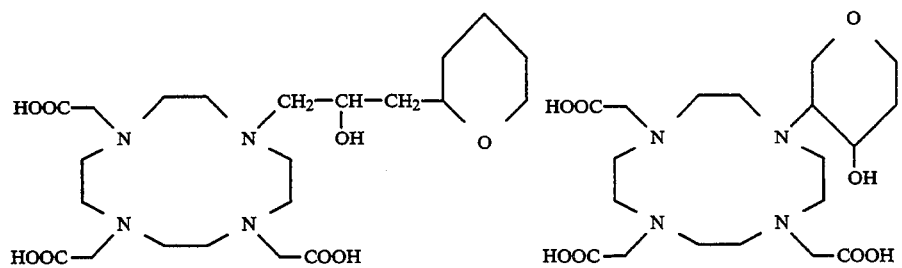
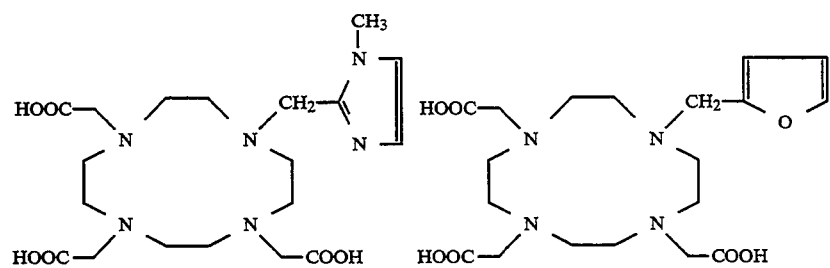
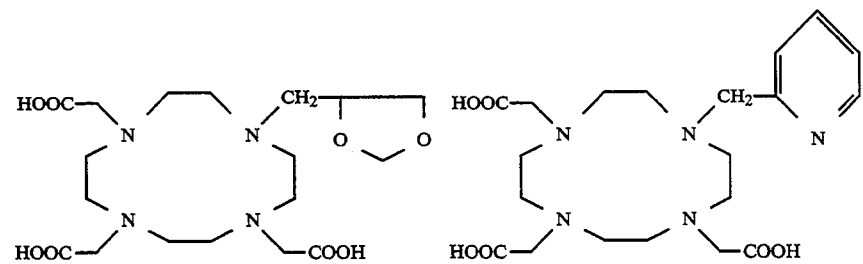
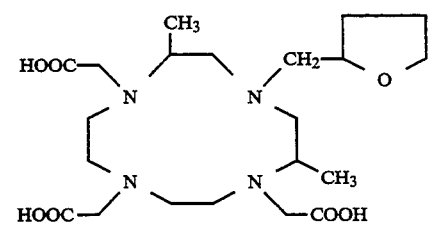

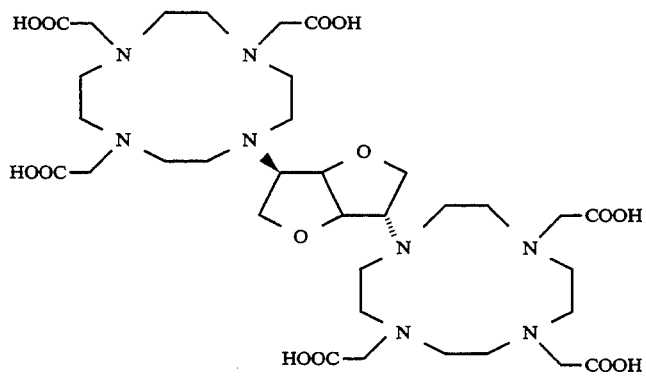

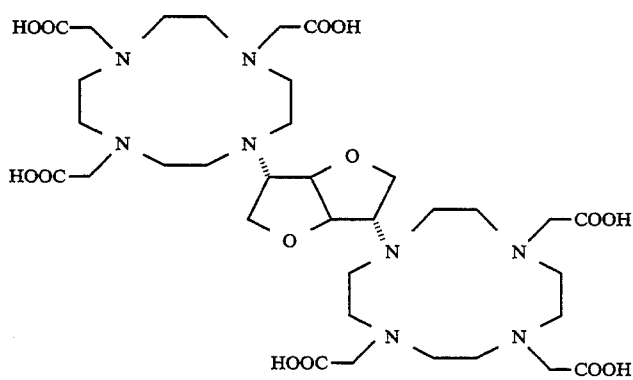

The macromolecules may be proteins, for example albumin, antibodies, in particular monoclonal antibodies, antibody fragments, azialoglycoproteins, or polymers, for example dextran or polylysine.

The ligands of formula I may be prepared by the following succession of steps:

a) reaction of a compound of formula:

W—NH$_2$   IV

W being as defined above, with a compound of formula

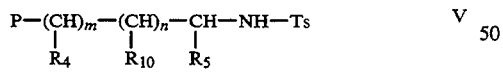

in which $R_4$, $R_5$, $R_{10}$, m and n are as defined above, P represents a leaving group chosen from mesyloxy and tosyloxy groups and Br, Cl and I atoms and Ts denotes the tosyl group, to give a compound of formula VII

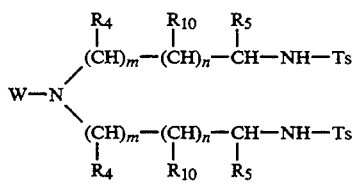

b) reaction of the compound of formula VII with a compound of formula VIII:

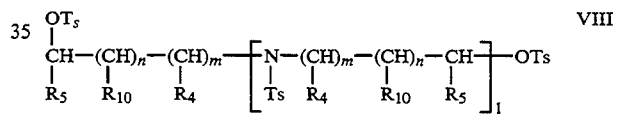

l being as defined above, in order to obtain a compound of formula IX

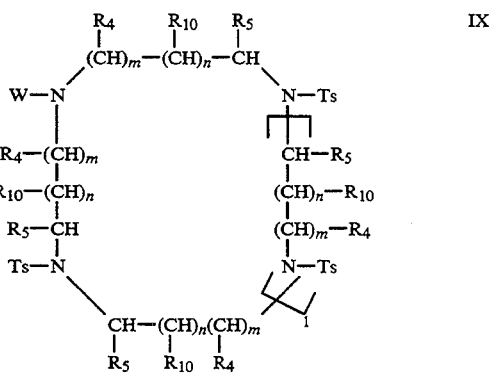

c) removal of the tosyl group, and
d) alkylation of the compound obtained.

The removal of the tosyl group may be effected, in particular, by reaction of the compounds of formula IX either with hydrobromic acid in acetic acid under reflux, as described in WO-8 602 352, or with concentrated sulphuric acid at about 100° C., as described in European Patent EP-287 465, or with sodium in liquid ammonia, as described in Helvetica Chimica Acta, vol. 71, 1988, p. 685 or with sodium in butanol at a temperature of about 100° C., as described in Helvetica Chimica Acta, vol. 73, 1990, p. 716.

The alkylation reaction may be carried out:
either directly by reaction of the compound obtained in step c) with chloroacetic acid or a chloroacetate, as described in European Patent EP-287 465,
or indirectly by reaction of the compound obtained in step c) with an ester of α-bromoacetic or α-chloroacetic acid, such as tert-butyl bromoacetate or tertbutyl chloroacetate, in DMAC or DMF in the presence of a base, as described in European Patent EP-299 795, or ethyl bromoacetate in ethanol in the presence of caesium carbonate, as described in J. Chem. Soc. Chem. Commun. 1989, p. 794, followed by a saponification of the compound obtained by means of a known saponification method or by means of trifluoroacetic acid in excess at ambient temperature in the case of the tert-butyl esters, as described in European Patent EP-299 795.

The group of compounds of general formula II as defined above may also be prepared by the following succession of steps:

a) reaction of a compound of formula

W—NH$_2$      IV in which W is as defined above, with a compound formula

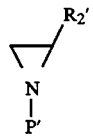

X in which R'$_2$ is as defined above and P' represents a tosyl, mesyl, phenylsulphonyl or 4-methoxyphenylsulphonyl group, in order to obtain a compound of formula XI

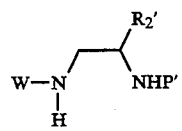

XI b) reaction of the compound of formula XI with a compound of formula XII

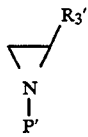

XII

R'$_3$ and P' being as defined above, in order to obtain the compound of formula XIII

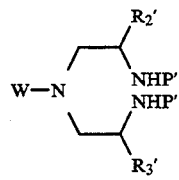

XIII c) reaction of the compound of formula XIII with a compound of formula

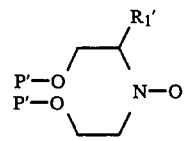

XIV

P' and R'$_1$ being as defined above, in order to obtain a compound of formula XV

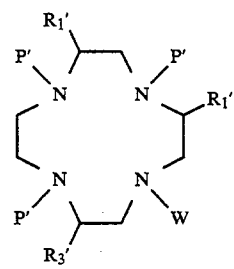

XV d) removal of the group P' in order to obtain the compound of formula XVI

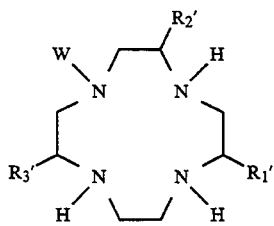

XVI and e) alkylation of the compound of formula XVI.

The reactions of steps a) and b) are carried out at a temperature of the order of 40° to 100° C. in a solvent such as DMF, toluene or acetonitrile.

The reaction of step c) takes place in DMF in the presence of NaH at elevated temperature, as described in Org. Synth. 1979, vol. 58, p. 86–97 or using caesium carbonate in dry DMF at a temperature of the order of 40° to 80° C., as described in J. Org. Chem. 1984, vol. 49, p. 110–113 or by phase transfer catalysis.

The reactions for removal of the group P' and alkylation take place as described above for the preparation of the compounds of formula I.

The compounds of formula XV may also be prepared in the following way:

a) reaction of benzylamine with a compound of formula X as described above in order to obtain a compound of formula XVII:

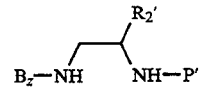

XVII

R$_z$ representing the benzyl group, b) reaction of the compound of formula XVII with a compound of formula XII as described above in order to obtain a compound of formula XVIII

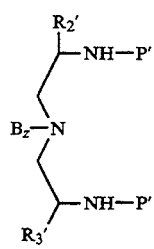　XVIII c) reaction of the compound of formula XVIII with a compound of formula XIV in order to obtain a compound of formula XIX

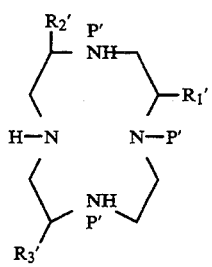　XIX d) hydrogenation of the compound XIX in order to obtain a compound of formula XX

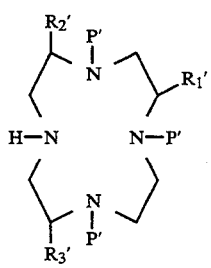　XX and e) reaction of the compound of formula XX with a compound of formula W—P", W being as defined above and P" representing the group P' or a chlorine or bromine atom, in order to obtain a compound of formula XV as described above.

The reactions for removal of the group P' and alkylation take place as described above for the preparation of the compounds of formula I.

The amines of formula IV are known products, such as, for example, 2-aminomethyl-1-ethylpyrrolidine, 2-aminoethyl-1-methylpyrrolidine, 2-aminomethylfuran, 2-aminomethyltetrahydrofuran and 2-methylaminopyridine, which products are marketed by Aldrich, or may be prepared, for example, in the following way:

a) epoxydation of a compound of formula XXI:

　XXI by means of chloroperbenzoic acid, as described in Journal of Pharmaceutic Sciences, 1970, vol. 59, p. 1676–1679, b) reaction of the compound obtained with a nitrite such as $NaN_3$ in aqueous methanol in the presence of ammonium chloride, as described in Tetrahedron Letters vol. 31, 1990, p. 5641–5644, in order to obtain a compound of formula XXII

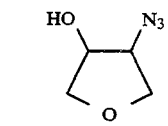　XXII c) reduction of the compound of formula XXII by means of hydrogen over palladised charcoal, as described in Synthesis 4, 1990, p. 366–368, in order to obtain the corresponding amine of formula XXIII

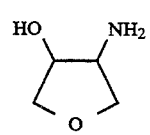　XXIII

The same procedure may be repeated for preparation of the following amines:

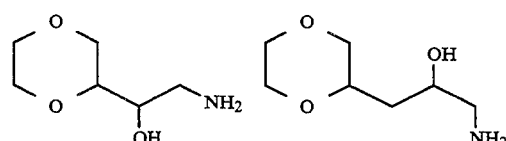

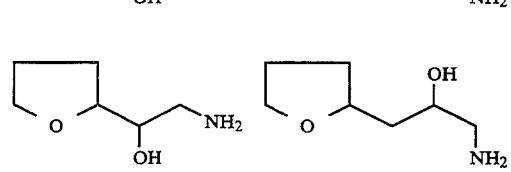

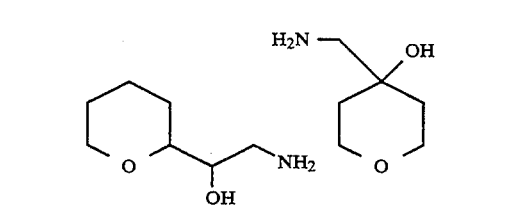

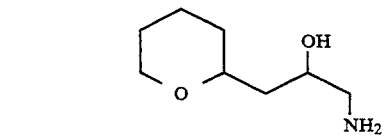

from the following compounds:

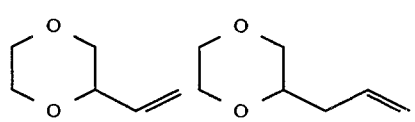

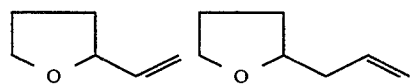

-continued

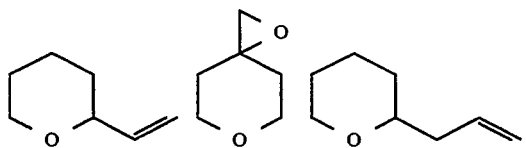

The preparation processes for these compounds are described in more detail by Normant and Castro, C. R. Acad. Sciences, 259, 1964, p. 830; Ficini, Bull Soc. Chim. Fr., 1956, p. 119–123; Mikailovic, Helv. Chim. Acta. vol. 56, No. 8, 1973, p. 3056; Colonge and Buendia, C.R. Acad. Sciences, 261, 1965; Olsen, Chem. Ber. vol. 91, 1958, p. 1589–1594.

The amine of formula

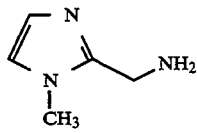

may also be prepared by reaction of 3-methylimidazole with formaldehyde, in order to obtain the compound of formula

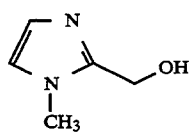

which is reacted with SOCl$_2$ in order to obtain

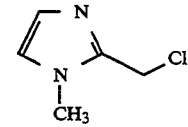

followed by a reaction of the product obtained with NAN$_3$, followed by a catalytic hydrogenation.

The compounds of formulae X and XII may be prepared by reaction of a compound of formula

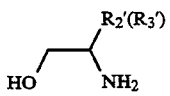 XXIV

R'$_2$ and R'$_3$ being as defined above, with a compound of formula P'—Cl, P' being as defined above, in order to obtain the compound of formula

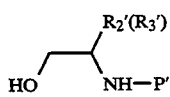 XXV which is reacted with aqueous KOH in order to obtain the corresponding compound of formula X or XII, as described in Helvetica Chimica Acta, vol. 68, 1985, p. 289, or by reacting a compound of formula

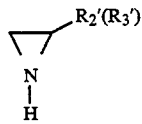

with tosyl chloride in the presence of pyridine so as to obtain a compound of formula

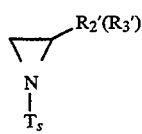

The dimers of formula I may be prepared by a process analogous to that described above, that is to say:

a) reaction of a compound of formula $$H_2N-W'-NH_2 \qquad (IVa)$$

W' representing a group

p, q, R$_{11}$ and R$_{12}$ being as defined above and X' representing a group chosen from:

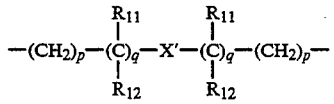

R'$_6$ and R'$_7$ forming, with the carbon atoms to which they are attached, a heterocycle, optionally composed of two fused rings, containing up to 12 members, 1 to 4 of which are heteroatoms chosen from oxygen, —N=,

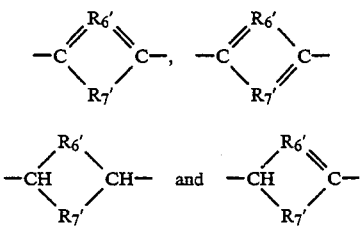

R$_8$ representing a hydrogen atom, a straight-chain or branched C$_1$–C$_6$ alkyl group, a straight-chain or branched C$_1$–C$_6$ hydroxyalkyl group, a straight-chain or branched C$_1$–C$_6$ polyhydroxyalkyl group or a straight-chain or branched C$_1$–C$_6$ alkoxy group, phosphorus and sulphur, the heterocycle being optionally substituted by one or more groups chosen from hydroxyl, mercapto, straight-chain or branched C$_1$–C$_6$ alkyl, straight-chain or branched C$_1$–C$_6$ hydroxyalkyl, straight-chain or branched C$_1$–C$_6$ polyhydroxyalkyl, straight-chain or branched C$_1$–C$_6$-alkoxy-C$_1$–C$_6$ alkyl, straight-chain or branched C$_1$–C$_6$-hydroxyalkoxy-C$_1$–C$_6$ alkyl and straight-chain or branched C$_1$–C$_6$ polyhydroxyalkoxy-C$_1$–C$_6$ alkyl groups, and a functional group enabling binding of the heterocycle to a macromolecule, with the proviso that when p and q are equal to 0, $R'_6$ and $R'_7$ represent a —$CH_2$—,

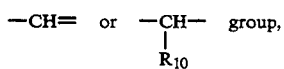

$R_{10}$ being as defined above; with a compound of formula V as defined above, to give a compound of formula VIIa:

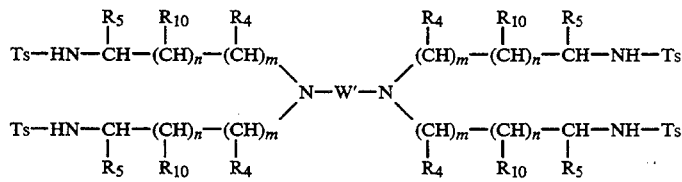

b) reaction of the compound of formula VIIa with a compound of formula VIII as described above in order to obtain a compound of formula IXa:

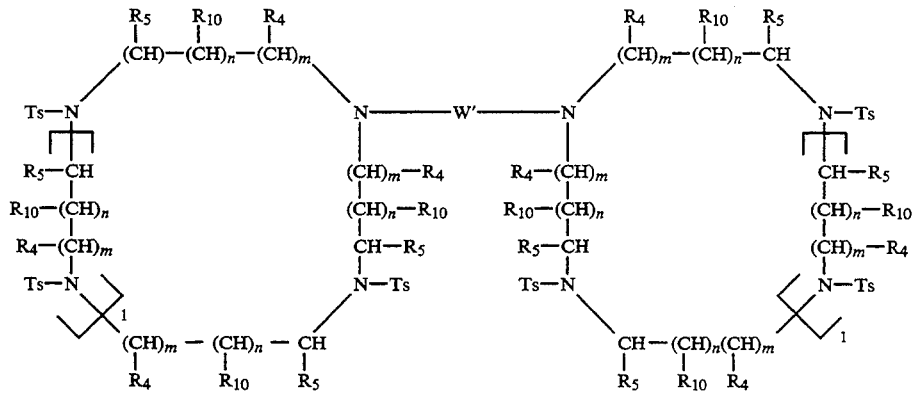

c) removal of the tosyl groups, and
d) alkylation of the compound obtained.

The present invention also relates to complexes formed by at least one ligand of formula I with at least one metal ion chosen from lanthanide ions, transition metal ions, barium, bismuth, lead and the radioisotopes $^{99m}TC$, $^{111}In$, $^{90}Y$, $^{64}Cu$ and $^{169}Yb$, as well as the salts of these complexes with pharmaceutically acceptable inorganic or organic bases or basic amino acids.

The complexes are monometallic or polymetallic, preferably monometallic or bimetallic, and neutral or ionic.

In these complexes, the metal ions are preferably gadolinium, europium, dysprosium, iron ($Fe^{3+}$), manganese ($Mn^{2+}$) and barium.

Examples of salts which may be mentioned are those formed with sodium hydroxide, N-methylglucamine, diethanolamine, lysine and arginine.

The complexes may be obtained by reaction of the ligands with a salt or an oxide of the metals in an aqueous solvent and, if appropriate, neutralisation to form a salt.

It is self-evident that the present invention encompasses not only the ligands of formula I and the complexes defined above in the form of a racemic mixture but also the stereoisomers of these ligands and complexes.

The complexes according to the invention formed by the ligands of formula I may be used in in-vitro and in-vivo diagnostic applications in man and in animals.

In nuclear magnetic resonance imaging and in in-vivo NMR spectroscopy they may be used as relaxation agents; for this purpose the complexes formed with the following metals are preferred: $Gd^{3+}$, $Mn^{2+}$ and $Fe^{3+}$; as magnetic susceptibility agents: for this purpose the complexes formed with the metals $Dy^{3+}$, $Ho^{3+}$, $Tb^{3+}$ and $Er^{3+}$ are preferred; or as chemical shift agents: for this purpose the complexes formed with the metals $Eu^{3+}$, $Pr^{3+}$ and $Yb^{3+}$ are preferred.

The complexes formed by the ligands of formula I and the metals preferably chosen from the lanthanides, $La^{3+}$, $Bi^{2+}$, $Ba^{2+}$ and $Pb^{2+}$ may be used in X-ray imaging.

In nuclear medicine, the complexes formed by the ligands of formula I and the metals $^{99m}Tc$, $^{111}In$, $^{64}Cu$ and $^{169}Yb$ may be used in radiodiagnostic applications and the complexes formed with the metals $^{90}Y$, $^{111}In$, $^{169}Yb$, $^{212}Bi$ and $^{64}Cu$ may be used in radiotherapeutic applications after coupling the complex to a suitable biomolecule.

The complexes formed by the ligands of formula i and the metal ions preferably chosen from $Eu^{3+}$ and $Tb^{3+}$ may be used in in vitro diagnostic applications using photoluminescence, such as immunofluoroescence assays.

The present invention consequently also relates to a diagnostic composition which can be administered to man, characterised in that it comprises at least one complex formed by a ligand of formula I with at least one metal ion chosen from lanthanide ions, transition metal ions, barium, bismuth, lead and the following radioisotopes $^{99m}Tc$, $^{111}In$, $^{90}Y$, $^{64}Cu$ and $^{169}Yb$, as well as the salts of these complexes with pharmaceutically acceptable inorganic or organic bases or basic amino acids, the complex optionally being coupled to a biomolecule or to a polymer or encapsulated in a liposome.

The invention also relates to a therapeutic composition containing a complex as defined above coupled to a biomolecule or to a polymer or encapsulated in a liposome.

These compositions may consist, in particular, of solutions of a complex according to the invention in a physiologically acceptable aqueous solvent.

Advantageously, a formulation of the compositions according to the invention contains, in addition to at least one complex according to the invention, from 0.05 to 10 mol % of the corresponding ligand in the form of the calcium or zinc complex.

The diagnostic compositions according to the invention may be administered:
  parenterally, including intravenously, intraarterially, intralymphatically and subcutaneously,
  orally,
  sub-arachnoidally, and
  intrabronchially in the form of an aerosol.

In magnetic resonance imaging, the doses are highly variable depending on the modes of administration.

For intravenous or intra-arterial administration, the dose is about 0.01 to 2 mM/kg.

For oral administration, this dose may range up to 10 mM/kg.

For the other modes of administration, the useful doses are generally lower than 1 mM/kg and for subarachnoidal administration are even generally lower than 0.05 mM/kg.

For use as chemical shift agents for in vivo spectroscopy, as magnetic susceptibility agents in NMR imaging and as contrast agents in X-ray radiology, the doses are the same, except in the case of intravenous or intraarterial administration, where the doses may be from 0.2 to 5 mM/kg.

The following examples illustrate the preparation of compounds according to the present application.

EXAMPLE 1

Preparation of the compound of formula:

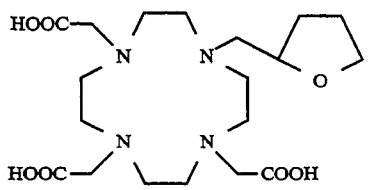

a) Preparation of the compound of formula:

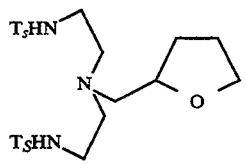

8.3 g (82 mmol) of tetrahydrofurfurylamine and 32.4 g (164 mmol) of tosylaziridine are dissolved in 500 cm³ of dry toluene at a temperature of 100° C. The mixture is stirred for 20 h at this temperature. The reaction mixture is then filtered hot and the solvent is evaporated. The oil obtained is filtered through a silica plug. After evaporation of the solvent, 28.4 g of a resinous product, which crystallises slowly, are obtained.

Yield: 70%. TLC: silica; CH₂Cl₂/ethyl acetate: 90/10; Rf: 0.3.

b) Preparation of the compound of formula:

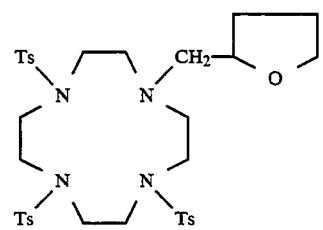

9.9 g (20 mmol) of product prepared in a) are dissolved in 1200 cm³ of dry DMF. Once the reactor has been placed under an argon atmosphere, 30 g of dry pulverulent Cs₂CO₃ are added and the mixture is heated to 30° C. A solution of 11.35 g of N-tosyl-bis(2-tosyloxyethyl)amine in 300 cm³ of DMF is introduced dropwise. The reaction mixture is stirred until the starting materials disappear. When the reaction is complete, the mixture is filtered and the solvent is evaporated under reduced pressure. The residue is taken up in 500 cm³ of dichloromethane. The chloromethylene solution is filtered and washed three times with water. After drying over MgSO₄, the dichloromethane is evaporated. The residue is purified by chromatography on silica. 7 g of pure product are obtained (yield: 49%).

TLC: silica; CH₂Cl₂/ethyl acetate: 95/5; Rf: 0.4

$^{13}$C NMR: 150–130 ppm, aromatic groups, tosyl groups; 80, 71.8, 53, 34.8 and 29.8 ppm, tetrahydrofurfuryl unit; 61–53 ppm, macrocycle; 26, 24 ppm, CH₃ of the tosyl groups.

C) Preparation of the compound of formula:

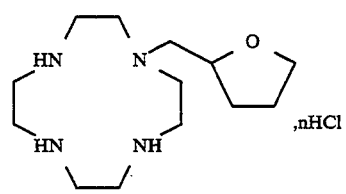

5 g of the product obtained in b) are added to 250 cm³ of dry n-butanol. The mixture is stirred under a dry nitrogen atomsphere and heated to a temperature of 100° C. After complete dissolution, 15 g of sodium are added to the solution in small portions. When the addition is complete, the butanol is evaporated and the residue is taken up in water. The aqueous solution is evaporated and the residue is taken up in absolute ethanol.

After evaporation of the ethanol, the product is taken up in dichloromethane and the salts are filtered off. The chloromethylene solution is evaporated and the oily residue obtained is dissolved in 200 cm³ of 1M hydrochloric acid. The acid solution is evaporated to dryness. After drying, 1.8 g of product in the form of the hydrochloride are obtained.

TLC: silica-dioxane/water/ammonia: 8/3/2; Rf: 0.1.

d) Preparation of the compound of formula:

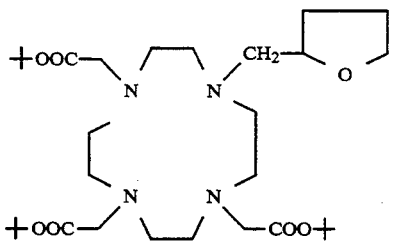

580 mg of the product prepared in c) and 1.5 g of sodium bicarbonate are suspended in 40 cm³ of dry DMF. The reactor is placed under an argon atmosphere and the mixture is heated to a temperature of 50° C. A solution of 1 cm³ of tert-butyl bromoacetate and 10 cm³ of dry DMF is then added dropwise. After 24 h, the DMF is evaporated under reduced pressure. The product is then dissolved in $CH_2Cl_2$ and the salts are separated off by filtration. After evaporation of the dichloromethane, a yellow oil is obtained which is purified by chromatography on silica. 650 mg of pure product, which crystallises slowly, are obtained.

TLC: silica; $CH_2Cl_2$/methanol 10%; Rf: 0.5. IR: 1710 cm$^{-1}$ carbonyl band. +H NMR: 1.43 ppm, singlet, tert-butyl. $^{13}$C NMR: 173 ppm, carbonyl; 83 ppm, quaternary C tertbutyl; 28 ppm, methyl groups; 74, 69, 30, 26 ppm, tetrahydrofuran unit. Mass spectrum: MH+ 599.

e) Preparation of the compound of formula:

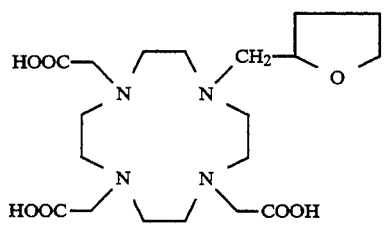

650 mg of the product prepared in d) are dissolved in 10 cm³ of trifluroacetic acid. The mixture is stirred for 24 h at ambient temperature. The trifluoroacetic acid is then evaporated and the residue is coevaporated with water. The product is then purified over an IRA 458 OH' resin. 150 mg of product are finally obtained.

TLC: silica; ethyl acetate/isopropanol/ammonia: 12/35/30; Rf: 0.6. $^{13}$C NMR: 170 ppm, carbonyl; 74, 65, 27, 22 ppm, tetrahydrofuran unit. Mass spectrum: MH+ 431.

The gadolinium complex of the compound described above is prepared by suspending $Gd_2O_3$ (4 mmol) and the crude compound obtained in the preceding example (8 mmol) in 100 ml of $H_2O$ at 80° C. and stirring the suspension for 24 hours.

The solution is cooled to ambient temperature and the solvent is then driven off under reduced pressure.

The resulting solid is dissolved in 15 ml of $H_2O$ and 5 ml of $C_2H_5OH$ and the solution is added dropwise to 750 ml of rapidly stirred acetone.

The precipitate which forms is filtered off and then washed with acetone and dried under vacuum at ambient temperature.

EXAMPLE 2

Preparation of the compound of formula:

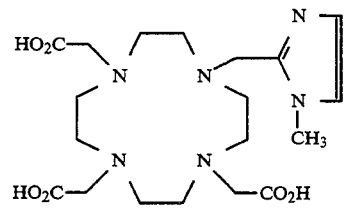

a) Preparation of the compound of formula:

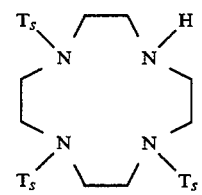

29 g (40 mmol) of monobenzyltritosylcyclene prepared according to the process described in European Patent EP-255 471 are reduced under a hydrogen pressure of $4 \times 10^5$ Pa in the presence of palladised charcoal in 500 cm³ of acetic acid. The mixture is stirred for 24 h at 70° C. After filtering, the solvent is evaporated. The solid obtained is washed successively with a potassium carbonate solution and then with water. 23.7 g of white powder are obtained.

TLC: $SiO_2$; $CH_2Cl_2/CH_3OH$ (95/5) Rf:=0.3; m.p.=195° C. Yield: 93% b) Preparation of the compound of formula

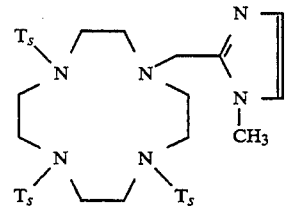

5 g (7.8 mmol) of tritosylcyclene prepared in a), 1.45 g (8.6 mmol) of 2-chloromethyl-1-methylimidazole, as described in P. C. Jocelyn, J.Chem. Soc., 3305, (1957), and 2.7 cm³ (19.7 mmol) of triethylamine are dissolved in 50 cm³ of dichloromethane. The reaction mixture is refluxed for 1 h. 1.45 g (8.6 mmol) of chlorinated reagent are added to the solution. The reaction mixture is refluxed for 12 h. 1.35 cm³ (9.85 mmol) of triethylamine dissolved in 10 cm³ of dichloromethane are added and the reaction mixture is refluxed for a further 12 h. After cooling, the triethylamine is removed by washing with water. The organic phase dried over $MgSO_4$ is concentrated and then purified by chromatography on silica. 6 g of white powder are obtained.

TLC: $SiO_2$; $CH_2Cl_2/CH_3OH$ (90/10) Rf:=0.6, Yield: 53%.

$^1$H NMR (DMSO) $\delta=2.41$ ppm; 2s, $CH_3$
$\delta=2.65$ ppm: m, $CH_2$
3.05 ppm$<\delta<3.7$ ppm: m, $CH_2$
6.7 ppm$<\delta<7.05$ ppm: d, CH=CH
7.4 ppm$<\delta<7.75$ ppm: m, CH=CH c) Preparation of the compound of formula:

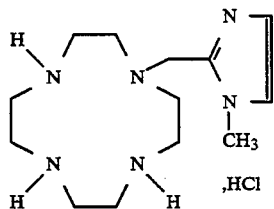

6 g (8.3 mmol) of the substrate prepared in b) are dissolved in 80 cm³ of dry n-BuOH. The solution, which is placed under an inert atmosphere, is heated to 100° C. 5 g (220 mmol) of sodium are added very slowly to the solution. The latter is then kept at 100° C. for 12 h. The solvent is evaporated. The product is taken up several times in water and dried before being extracted with dichloromethane (three times 20 cm³). The solvent is evaporated and the residue dissolved in 50 cm³ of 6N hydrochloric acid. The solution is concentrated and washed three times with 15 cm³ of dichloromethane. After drying, 2.9 g of product are isolated in the form of the hydrochloride.

TLC: SiO₂; CHCl₃/CH₃OH/NH₄OH (4/4/2). Rf:=0.3.

d) Preparation of the compound of formula:

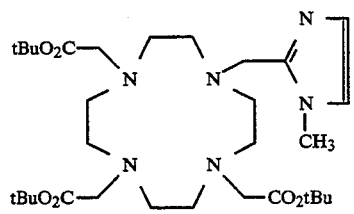

2.2 g (5.8 mmol) of product prepared in c) and 6.3 g (58 mmol) of sodium carbonate are suspended in 35 cm³ of dry DMF. The mixture is placed under an inert atmosphere and heated to 60° C. 3.75 g (19.2 mmol) of tert-butyl bromoacetate dissolved in 35 cm³ of DMF are added dropwise. After a reaction time of 24 h, the DMF is evaporated. The product is taken up in 100 cm³ of dichloromethane and washed three times with 70 cm³ of water. The organic phase is dried over MgSO₄, concentrated and purified by chromatography on silica. After evaporation of the solvent and drying, 1.4 g of white powder are isolated. Yield 40%.

TLC: SiO₂; CH₂Cl₂/EtOH (90/10); Rf:=0.5. IR (KBr): 1720 cm⁻¹ C=O.

H⁺ NMR (DMSO): $\delta = 1.4$ ppm: 2s, C(CH₃)₃
$2 < \delta < 3.5$ ppm: m, CH₂=CH
$6.5 < \delta < 7.05$ ppm: d, CH=CH ¹³C NMR (DMSO): $\delta = 27.4$ ppm, CH₃
$\delta = 31.7$ ppm, CH₃
$\delta = 48.9$ ppm, CH₂
$\delta = 55.0$ ppm, CH₂
$\delta = 55.7$ ppm, CH₂
$\delta = 80.9$ ppm, C
$\delta = 121.0$ ppm, HC=CH
$\delta = 125.5$ ppm, HC=CH
$\delta = 146.0$ ppm, C=N
$\delta = 171.6$ ppm, C=O
$\delta = 172.3$ ppm, C=O Mass spectrum (FAB) M=632 (M+Na⁺) Z e) preparation of the compound of formula:

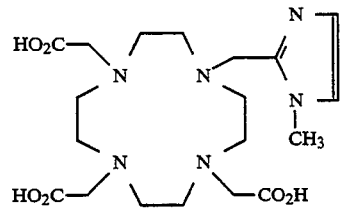

1 g (1.64 mmol) of the product prepared in d) is dissolved in 40 cm³ of trifluoroacetic acid. The solution, which is placed under an inert atmosphere, is stirred for 20 h at ambient temperature- The trifluoroacetic acid is then evaporated and then removed as an azeotrope with water. The crude product is purified over an IRA 458 resin. 600 mg of white powder are isolated. Yield 83%

TLC: SiO₂; AcOEt/isopropanol/NH₄OH; Rf=0.5.
IR (KBr) 3450 cm⁻¹ OH 1650 cm⁻¹ C=O
H⁺ NMR (DMSO) $2.6 < \delta < 4$ ppm: m; CH₂ and CH₃
$6.8 < \delta < 7.1$ ppm: d; CH=CH
$\delta = 7.4$ ppm: m; OH
¹³C NMR (DMSO) $\delta = 32.7$ ppm, CH₃
$\delta 49.6$ ppm, CH₂
50.7 ppm, CH₂
51.2 ppm, CH₂
54.8 ppm, CH₂
122.0 ppm, CH=CH
125.7 ppm, CH=CH
144.0 ppm, C=N
170.1 ppm, 2C=O
$\delta = 171.1$ ppm, 1C=O

EXAMPLE 3

Preparation of the compound of formula:

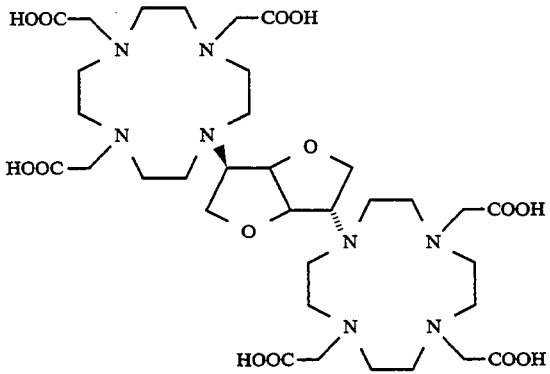

a) Preparation of 2:5-ditosyl-1,4:3,6-dianhydrosorbitol of formula:

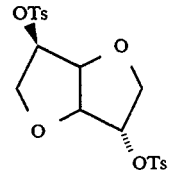

2:5-Ditosyl-1,4:3,6-dianhydrosorbitol is prepared from 1,4:3,6-dianhydro-D-sorbitol, which is commercially available under the name Isosorbide ® from Aldrich Chimie (Strasbourg), in accordance with the method described in J. Am. Chem. Soc. 68 (1946) p. 927 and J. Chem. Soc. (1946) p. 393.

Mass obtained per 100 g of Isosorbide ®: 213 g; yield: 69%. TLC: $SiO_2$, eluent $CH_2Cl_2/AcOEt$: 97/3, Rf: 0.6.

b) Preparation of 2:5-diazido-1,4:3,6-dianhydrosorbitol.

2:5-Diazido-1,4:3,6-dianhydrosorbitol is prepared from the compound obtained in the preceding step according to the method described in Carbohydrate Research 85 (1980) p. 259.

Mass obtained per 150 g of the compound from the preceding step: 37 g; yield 57%; TLC: $SiO_2$; eluent: petroleum ether/ethyl ether: 85/15;

Rf: 0.25

IR: 2100 $cm^{-1}$; azide band.

c) Preparation of 2:5-diamino-1,4:3,6-dianhydrosorbitol.

4.5 g (22.95 mmol) of the compound obtained in the preceding step are dissolved in 200 $cm^3$ of ethanol at 95° C. 1 g of palladised charcoal is added to the solution and the suspension is then placed in an autoclave under a hydrogen pressure of $13-14 \times 10^5$ Pa, at a temperature of 50° C. The reaction mixture is stirred for 7 hours under constant hydrogen pressure and is then left to stand overnight under residual hydrogen pressure.

The reaction mixture is filtered and the solvent evaporated. The oily residue obtained is taken acetonitrile and the white precipitate formed is removed by filtering off.

The solution obtained is evaporated to give 3.3 g of a colourless oil.

Yield: 100%.

IR: disappearance of the azide band at 2100 $cm^{-1}$. NH bands at 3360 and 3280 $cm^{-1}$.

$^{13}C$ NMR: 55.67 ppm—59.17 ppm—72.41 ppm—75.58 ppm-82.33 ppm—92.68 ppm.

TLC: $SiO_2$; eluent $CH_2Cl_2/MeOH/NH_3$: 16/4/0.1. Rf =0.37.

d) Preparation of the compound of formula:

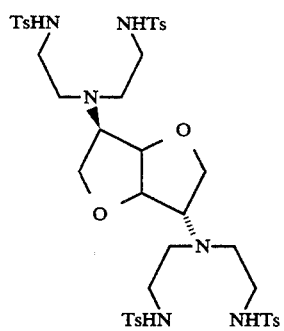

5 g (34.7 mmol) of the compound obtained in the preceding step and 27.3 g (0.139 mol) of tosylaziridine dissolved in 250 $cm^3$ of acetonitrile are introduced into a 500 $cm^3$ three-necked round-bottomed flask. The mixture is stirred and heated to 70° C. for 4 days. The solvent is evaporated under reduced pressure and the residue purified on a silica column.

17 g of the expected product are obtained in a yield of 52%.

TLC: $SiO_2$; $CH_2Cl_2/MeOH$: 95/5. Rf=0.35. IR: 3250 $cm^{-1}$; H—N—Ts.

e) Preparation of the compound of formula:

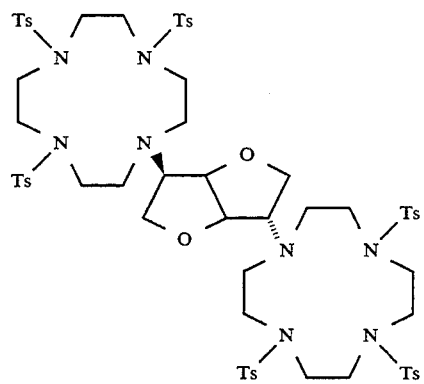

15 g (16.1 mmol) of the compound obtained in the preceding step, 750 $cm^3$ of dry DMF and 32 g of anhydrous $Cs_2CO_3$ are introduced into a 2 l three-necked round-bottomed flask placed under an argon atmosphere. A solution of 18.25 g (32.18 mmol) of tosylated bis-ethanolamine in 200 $cm^3$ of DMF is added slowly. The mixture is heated at 40° C. for 3 days. The solution is filtered and the DMF is evaporated. The compound is purified on a silica column.

8 g of the title product are obtained in a yield of 36%.

TLC: $SiO_2$ $CH_2Cl_2/AcOEt$: 90/10, Rf=0.65. $^1H$ NMR: 7.4–7.8 ppm, multiplet: aromatic H, H from tosyl groups, 2.4 ppm, singlet: methyl, tosyl.

f) Preparation of the compound of formula

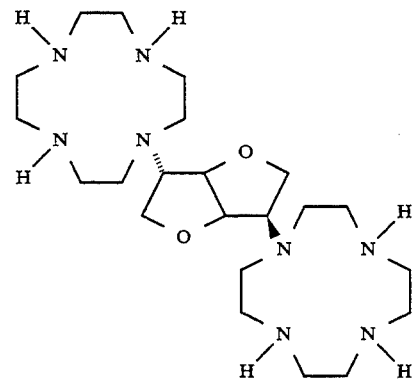

4 g (2.91 mmol) of the product obtained in the preceding step are introduced into 350 $cm^3$ of dry n-butanol. The mixture is heated to 110° C., with stirring. The reactor is purged with dry nitrogen and 20 g of Na are added in small portions over a period of 8 hours.

The temperature is then reduced to 80° C. and the reaction mixture is stirred overnight.

After complete removal of the butanol, the oily residue is taken up in aqueous 1M HCl. The solution is filtered and washed with dichloromethane.

After evaporation, the amine hydrochloride is recovered in the form of a white solid.

2g of product are obtained.

TLC: $SiO_2$; $CH_2Cl_2/MeOH/aqueousNH_4$: 4/4/2, flame having origin Rf=0. $^{13}C$ NMR: 40.72 ppm–48.42 ppm, H of the macrocycles, 63.89 ppm–66.03 ppm–66.40 ppm–70.16 ppm–82.05 ppm–83.25 ppm, central bisheterocycle unit.

g) Preparation of the compound of formula:

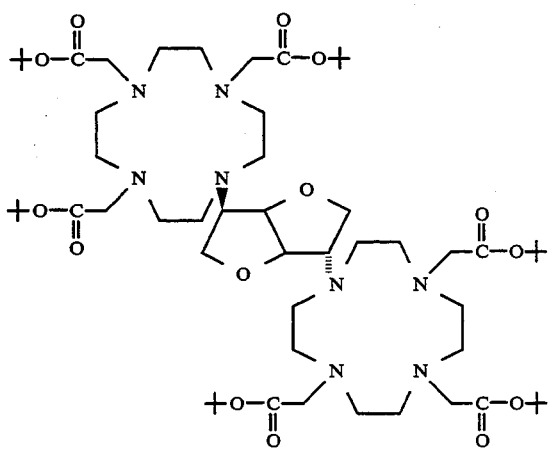

3.9 g of the product obtained in the preceding step in 45 cm³ of acetonitrile are introduced into a 500 cm³ three-necked round-bottomed flask fitted with a condenser and a magnetic bar stirrer and placed under argon.

15 g of anhydrous sodium carbonate are added with 40 cm³ of acetonitrile.

The mixture is stirred and heated to 40° C.

A solution of 10.8 g of tert-butyl bromoacetate in 30 cm³ of acetonitrile is then added dropwise.

The mixture is filtered after 24 hours and the reaction solution is concentrated. The oil obtained is taken up in ethyl ether.

The solid obtained is washed several times with ether. After purification on a silica column, 5.6 g of the title compound are obtained.

TLC: SiO₂; CH₂Cl₂/MeOH:90/10, Rf=0.4 FAB mass spectrum (glycerol MH⁺ Na⁺ 1162 h) Preparation of the compound of formula:

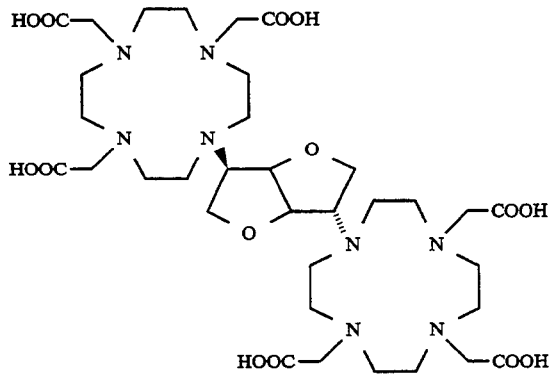

The product obtained in the preceding step is dissolved in 30 cm³ of trifluoroacetic acid.

The reaction mixture is stirred at ambient temperature for 16 hours. The solvent is evaporated and the residue is taken up in water.

The solution obtained is concentrated. The product is purified over IRA 458 resin.

TLC: SiO₂; AcOEt/isopropanol/aqueous ammonia: 12/35/30 Rf=0.25+0.42.

FAB mass spectrum (glycerol), MH+ 803. ¹³C NMR: 171.9 ppm–171.6 ppm–167.4 ppm, carbonyls; 57.55 ppm–61.23 ppm –62.57 ppm–68.80 ppm–79.18 ppm–80.10 ppm: central heterocyclic system; 53.9 ppm:

methylene from the carboxymethyls; 50.62 ppm–41.64 ppm: macrocycles.

EXAMPLE 4

Preparation of the compound of formula:

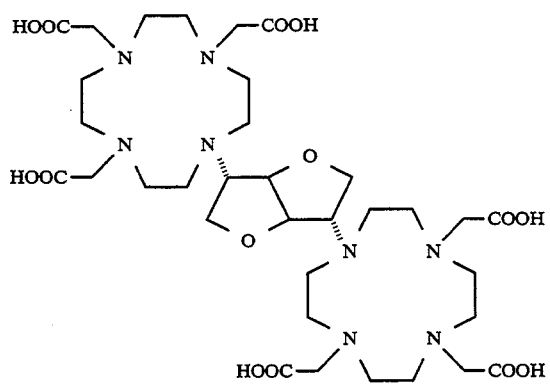

a) Preparation of 2:5-ditosyl-1,4:3,6-dianhydromannitol of formula:

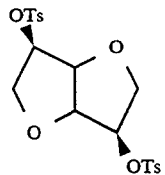

The title product is prepared from 73 g (0.5 mol) of 1,4:3,6-dianhydro-D-mannitol, which is available commercially under the name Isomannide ® from Aldrich Chimie (Strasbourg), according to the method described in Journal of Organometallic Chemistry 253 (1983) 249–252.

Mass obtained=196.2g; Yield: 86.5%.

b) Preparation of 2:5-diazido-2,5-dideoxy-1,4:3,6-dianhydroiditol.

The title compound is prepared from 98 g (0.2 mol) of the compound obtained in the preceding step according to the method described in Carbohydrate Research 85 (1980) 259–269.

Mass obtained: 36 g (yield: 85%).

c) Preparation of 2:5-diamino-2,5-dideoxy-1,4:3,6-dianhydroiditol.

The title compound is obtained from 12 g (0.06 mol) of the compound from the preceding step according to the methods described in JACS 78 (1956) 3180 and Synthetic Communications 19 (1989) 1493–1498.

Mass obtained: 9 g.

d) Preparation of the compound of formula:

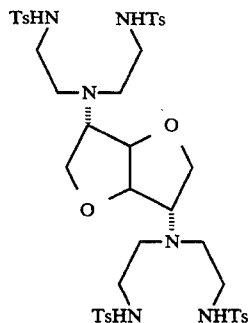

8.8 g (0.06 mol) of the compound obtained in the preceding step are dissolved in 800 ml of acetonitrile in the presence of 48.15 g (0.244 mol) of N-tosylaziridine.

The reaction mixture is refluxed for 48 ho The mixture is evaporated to dryness for subsequent column chromatography. 26.1 g of product are thus obtained, which is a yield of 51%.

TLC (CH$_2$Cl$_2$ 95/AcOEt 5/MeOH 5): Rf=0.5. $^1$H NMR (200 MHz) (DMSO): 2.3 ppm, CH$_3$ tosyl 7.3 and 7.6 ppm, aromatic H. $^{13}$C NMR 128, 130, 138 and 143 ppm, aromatic C, 85, 70, 68 ppm, C from the central bisheterocyclic system, 22 ppm, C from the CH$_3$ of the tosyl group.

e) Preparation of the compound of formula

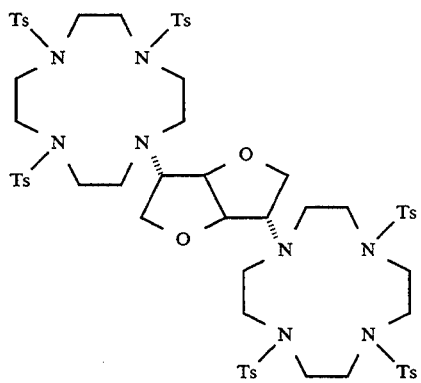

30 g of the product obtained in the preceding step (0.0323 mol) are dissolved in 1.8 l of anhydrous DMF in the presence of 94 g of Cs$_2$CO$_3$, under argon, at 40° C. One hour later a solution of 36.6 g (0.0645 mol) of tritosylated diethanolamine in 0.9 l of DMF is added slowly to this suspension.

The reaction mixture is heated at 40° C. for 48 h. After filtering and evaporating off the DMF, the residue obtained is chromatographed on a column.

16 g of product are thus obtained, which is a yield of 36%.

TLC: SiO$_2$; CH$_2$Cl$_2$ 95/AcOEt 4/MeOH 1; Rf=0.15. IR (KBr disc): disappearance of the band characteristic of the NH-Ts bond at 3300 cm$^{-1}$. $^{13}$C NMR (200 MHz) (DMSO): 128, 130, 138 and 143 ppm, aromatic C, 83.68 and 66 ppm, C from the central bis-heterocyclic system, 75 ppm and unresolved bands at 50 ppm, C from the two rings formed, 22 ppm, tosyl CH$_3$.

f) Preparation of the compound of formula:

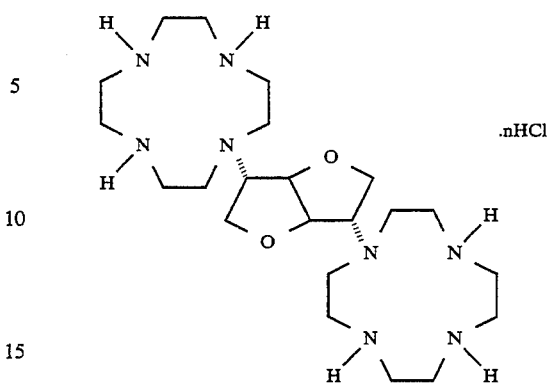

16 g (0.0116 mol) of the product obtained in the preceding step are dissolved in 840 ml of n-butanol previously heated to reflux. 73.6 g (3.2 mols) of sodium cut into pieces are added slowly to this solution. The reaction mixture is heated at 80° C. for 12 h. After complete removal of the solvent, the product is taken up in 300 ml of hydrochloric acid. The solution obtained is washed twice with CH$_2$Cl$_2$. The aqueous phase is evaporated to dryness. 7.0 g of the expected product are obtained, which is a yield of 90%.

TLC: SiO$_2$; CH$_2$Cl$_2$ 4/MeOH 4/NH$_4$OH 2: Rf=0.1 (development with I$_2$). $^{13}$C NMR (DMSO): 83.68 and 66 ppm, C from the central heterocyclic system, 44, 42, 38 and 37 ppm, C from the bicyclic radical.

g) Preparation of the compound of formula:

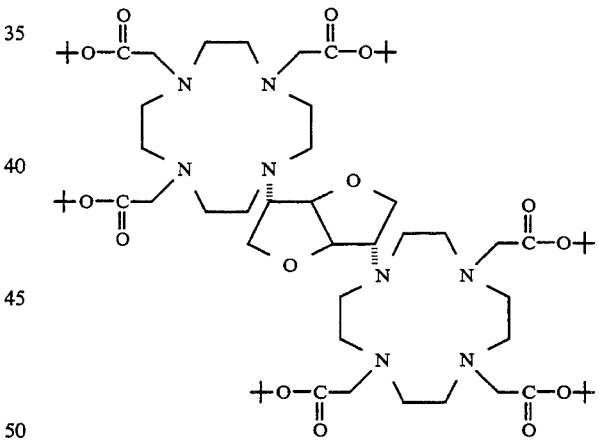

6 g (0.00886 mol) of the product obtained in the preceding step are suspended in 150 ml of CH$_3$CN at 40° C. in the presence of 18.8 g (0,177 mol) of Na$_2$CO$_3$. A solution of 13.8 g (0.070 mol) of BrCH$_2$COOtBu in 80 ml of CH$_3$CN is added dropwise to the mixture. The reaction mixture is heated at 40° C., with stirring, for 72 hours. After filtering, the solution is concentrated. The expected product crystallises out. After filtering off and washing with ether, 8.3 g of the expected product are obtained, which is a yield of 77%.

TLC: SiO$_2$; CH$_2$Cl$_2$ 85/MeOH 15: Rf=0.6. IR: 1710 cm$^{-1}$, carbonyl band. $^1$H NMR: 1.4 ppm singlet, tert-butyl group. $^{13}$C NMR (DMSO): 175 ppm, C from the carbonyl group, 85 ppm, quaternary C from the tert-butyl group, 27 ppm, CH$_3$, 63.68 and 80 ppm, central bisheterocyclic system.

h) Preparation of the compound of formula:

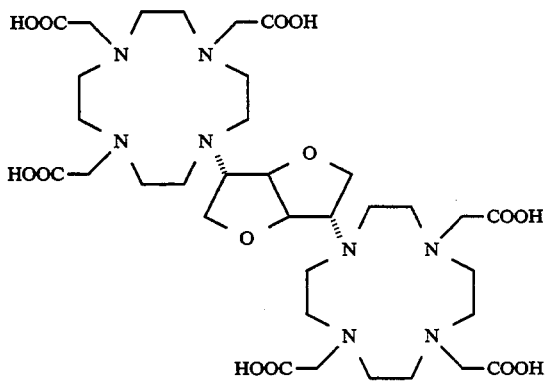

0.3 g (0.0073 mol) of the product obtained in the preceding step are dissolved in 130 ml of CF$_3$COOH at ambient temperature. After a reaction time of 12 h, the reaction mixture is concentrated and then taken up in water and evaporated.

The product is purified over IRA 458 resin.

TLC: SiO$_2$; AcOEt 12/isopropanol 35/NH$_4$OH 30: Rf=0.2+0.35. $^{13}$C NMR: 167 and 172 ppm, acid C, 63, 68 and 80 ppm, central heterocyclic system, 54 ppm, CH$_2$ in the α-position with respect to COOH, 40<δ<50 ppm multiplet, C from the two rings. FAB mass spectrum (glycerol), MH+ 803.

EXAMPLE 5

Preparation of the compound of formula:

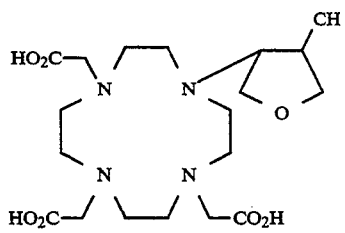

a) Preparation of 3,4-epoxytetrahydrofuran

The title product is obtained from 58 g (0.83 mol) of 2,5-dihydrofuran, which is available commercially from Aldrich Chimie (Strasbourg), according to the method described in Journal of Pharmaceutical Sciences 59 (1970) 1676–1679.

Mass obtained: 54 g. Yield: 71%.

b) Preparation of 3-hydroxy-4-azidotetrahydrofuran.

The title product is obtained from 54 g (0.63 mol) of the product obtained in the preceding step, according to the method described in Tetrahedron Letters 3 (1990) 5641–5644.

Mass obtained: 73 g; yield 90%.

c) Preparation of 3-hydroxy-4-aminotetrahydrofuran.

The title compound is obtained from 24 g (0.19 mol) of the product from the preceding step, according to the method described in Synthesis 4 (1990) 366–368.

Mass obtained: 20 g.

d) Preparation of the compound of formula:

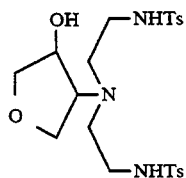

10 g (0.097 mol) of the product from the preceding step are mixed with 38.2 g (0.19 mol) of N-tosylaziridine in 600 ml of acetonitrile at 50° C. for 72 hours. The solution is concentrated and the residue obtained is then crystallised from an ethyl acetate/toluene mixture.

After filtering off, washing and drying, 31 g of product are obtained, which is a yield of 64%.

TLC: SiO$_2$; CH$_2$Cl$_2$ 90/MeOH 10: Rf=0.5. $^1$H NMR (200 MHz) (DMSO): 2 doublets at 7.4 and 7.7 ppm, aromatic protons, 5 ppm, OH, protons of the heterocycle: singlet at 4 ppm, multiplet at 3.7 ppm, multiplet at 3.4 ppm, 2<δ<3 ppm, CH$_2$—CH$_2$ and CH$_3$ (T$_s$).

e) Preparation of the compound of formula:

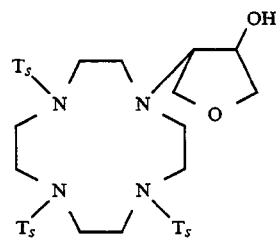

18 g (0.0362 mol) of the product from the preceding step are dissolved in 1200 ml of DMF in the presence of 54 g (0.165 mol) of caesium carbonate, at a temperature of 40° C. under argon.

A solution of 20.6 g (0.0363 mol) of tritosylated diethanolamine is added in 600 ml of DMF.

After the end of the reaction, the reaction mixture is filtered and then concentrated.

The residue is chromatographed on a column.

15 g of product are obtained, yield: 58%.

TLC: SiO$_2$; CH$_2$Cl$_2$ 95/MeOH 5: Rf=0.2. IR (KBr) 3300 cm$^{-1}$, NHTs. $^1$H NMR (DMSO) aromatic protons: 7.6 ppm triplet, 7.4 ppm doublet, 5.1 ppm, doublet, OH; Tetrahydrofuran protons: 4.1 ppm, singlet, 2<δ<3.9 ppm unresolved bands.

f) Preparation of the compound of formula:

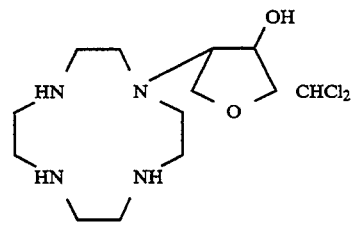

20.5 g (0.028 mol) of the product from the preceding step are dissolved in 440 ml of n-butanol under reflux.

32.0 g (1.4 mols) of sodium in pieces are added slowly. The reaction mixture is then heated to a temperature of 80° C., with stirring.

After removal of the butanol using water, the residue is taken up in 300 ml of 1N HCl. The solution obtained is washed with CH$_2$Cl$_2$ and then evaporated to dryness.

9 g of product are obtained;

TLC: SiO$_2$; CH$_2$Cl$_2$ 4/MeOH 4/NH$_4$OH 2: Rf=0.1 (I$_2$) $^{13}$C NMR: 84–72–69 and 67 ppm, tetrahydrofuran C; 45 and 42 ppm, ring C.

g) Preparation of the compound of formula:

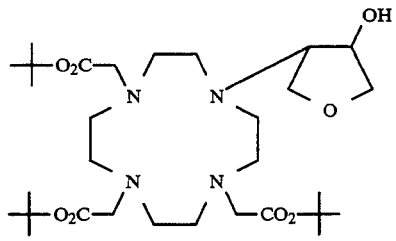

54 g (0.147 mol) of the product from the preceding step are suspended in 1.5 l of acetonitrile, in the presence of 155.5 g (1.46 mol) of Na$_2$CO$_3$, at a temperature of 40° C.

A solution of 114.5 g (0.6 mol) of tert-butyl bromoacetate in 0.7 l of acetonitrile is added slowly. The reaction mixture is then filtered and the filtrate evaporated to dryness. The residue obtained is crystallised in ethyl ether and then chromatographed on column. 69 g of the product are obtained. Yield: 72%.

TLC: SiO$_2$; CH$_2$Cl$_2$ 80/MeOH 20; Rf=0.6. IR (KBr) 1710 cm$^{-1}$, C=O. $^{13}$C NMR: 170 and 173 ppm, carbonyl C, 81 ppm, quaternary C, 84, 72, 69 and 67 ppm, tetrahydrofuran 55 ppm, C of the CH$_2$ in the α-position of the ester, 52, 49 and 46 ppm, ring C, 28 ppm, CH$_3$ of the tert-butyl.

h) Preparation of the compound of formula:

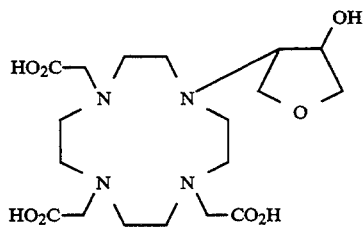

38 g (0.063 mol) of the product from the preceding step are dissolved in 600 ml of trifluoroacetic acid at ambient temperature.

After 18 hours, the reaction mixture is concentrated to dryness and the residue is then taken up in water. After purification over IRA 458 resin, 20 g of product are obtained. Yield: 73%.

TLC: SiO$_2$; AcOEt 12/isopropanol 35/NH$_4$OH 30: Rf=0.45 and 0.5.

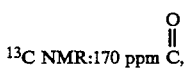
$^{13}$C NMR:170 ppm C, 73, 72, 69 and 67 ppm, tetrahydrofuran C, 55 ppm, C of the CH$_3$ in the α-position with respect to COOH, 55 ppm δ<45 ppm, ring C. Mass spectrum: FAB (glycerol) MH$^+$ 433.

EXAMPLE 6

Preparation of the compound of formula

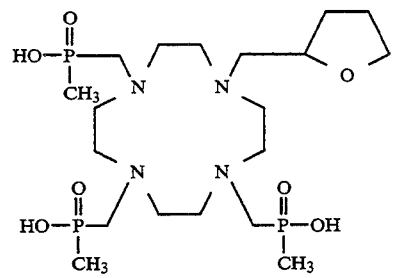

a) Preparation of the compound of formula:

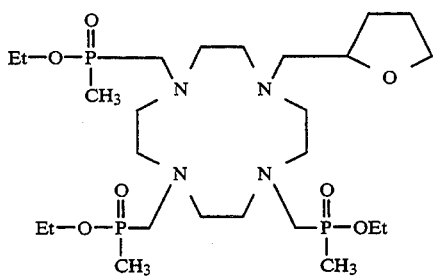

0.7 g (2.7 mmol) of the compound obtained in step c) of Example 1 above, 0.7 g of paraformaldehyde and 2.5 g (16.2 mmol) of diethyl methyl phosphite, obtained according to the method described in Organic Preparations and Procedures Int. 11(1) 11–16 (1979) in 30 ml of THF are refluxed for 12 hours.

After evaporation, the solution is chromatographed on alumina, eluting with dichloromethane.

0.5 g of a pale yellow oil is obtained, which is a yield of 30%.

TLC: SiO$_2$; CH$_2$Cl$_2$/MeOH: 90/10; Rf=0.2.

b) Preparation of the compound of formula:

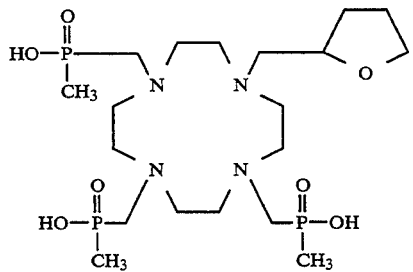

0.5 g (0.8 mmol) of the compound obtained in the preceding step in 25 ml of 6N HCl is refluxed for 12 hours.

After evaporation, the product is purified on silanised silica.

0.25 g of the title compound are obtained, which is a yield of 42%.

TLC: SiO$_2$; dioxan/water/NH$_3$: 8/3/2; Rf: 0.1.

We claim:

1. Ligands of formula I

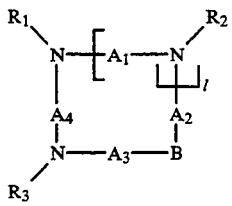

in which

A$_1$, A$_2$, A$_3$ and A$_4$, which may be identical or different, independently of one another represent a group:

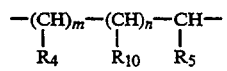

m and n being identical or different integers such that the sum of m and n is between 1 and 5, R$_4$ and R$_5$, which may be identical or different, represent a hydrogen atom, a straight-chain or branched C$_1$-C$_6$ alkyl group, a straight-chain or branched C$_1$-C$_6$ hydroxyalkyl or polyhydroxyalkyl group, a functional group enabling the macrocycle of formula I to be attached to a macromolecule, a straight-chain or branched C$_1$-C$_6$ alkoxy -C$_1$-C$_6$ alkyl group, a straight-chain or branched hydroxy -C$_1$-C$_6$ alkoxy -C$_1$-C$_6$ alkyl group or a straight-chain or branched polyhydroxy -C$_1$-C$_6$ alkoxy -C$_1$-C$_6$ alkyl group, an aryl group or an aryl group substituted by one or more identical or different substituents chosen from a halogen atom, a hydroxyl group, a nitro group or a C$_1$-C$_6$ alkyl, C$_1$-C$_6$ hydroxyalkyl, C$_1$-C$_6$ polyhydroxyalkyl, C$_1$-C$_6$ alkoxy or C$_1$-C$_6$ alkoxy-C$_1$-C$_6$ alkyl group, an aralkyl group or an aralkyl group substituted by one or more identical or different substituents chosen from a halogen atom, a hydroxyl group, a nitro group or a C$_1$-C$_6$ alkyl, C$_1$-C$_6$ hydroxyalkyl, C$_1$-C$_6$ polyhydroxyalkyl, C$_1$-C$_6$ alkoxy or C$_1$-C$_6$ alkoxy-C$_1$-C$_6$ alkyl group, the alkyl radical of the aralkyl group being C$_1$—C$_6$ and straight-chain or branched, R$_{10}$ represents the group R$_4$ or R$_5$, a hydroxyl group or a C$_1$-C$_6$ alkoxy group, R$_1$, R$_2$ and R$_3$, which may be identical or different, are chosen from a hydrogen atom and the

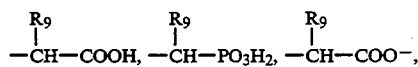

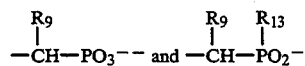

groups, R$_9$ representing a hydrogen atom, a straight-chain or branched C$_1$-C$_6$ alkyl group, a straight-chain or branched C$_1$-C$_6$ hydroxyalkyl group, a straight-chain or branched C$_1$-C$_6$ polyhydroxyalkyl group or a straight-chain or branched C$_1$-C$_6$ alkoxy-C$_1$-C$_6$ alkyl group and R$_{13}$ representing a straight-chain or branched C$_1$-C$_6$ alkyl group, a straight-chain or branched C$_1$-C$_6$- hydroxyalkyl or -polyhydroxyalkyl group, a straight-chain or branched C$_1$-C$_6$ alkoxy -C$_1$-C$_6$ alkyl group or a straight-chain or branched C$_1$-C$_6$ hydroxyalkoxy- or -polyhydroxyalkoxy- C$_1$-C$_6$ alkyl group, B represents the group

W representing the group

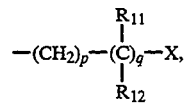

in which p and q are identical or different integers from 0 to 6, R$_{11}$ and R$_{12}$, which may be identical or different, have the same meaning as R$_{10}$ when p is other than 0 and have the same meaning as R$_4$ and R$_5$ when p is equal to 0 and X represents a group

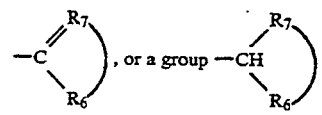

R$_6$ and R$_7$ forming, with the carbon atom to which they are attached, a heterocycle, containing up to 12 members, selected from thienyl, dihydrothienyl, tetrahydrothienyl, furyl, dihydrofuryl, tetrahydrofuryl, pyranyl, dihydropyranyl, tetrahydropyranyl, pyrrolyl, 2H-pyrrolyl, dihydropyrrolyl, tetrahydropyrrolyl, imidazolyl, pyrazolyl, pyridyl, pyrazinyl, pyrimidinyl, pyridazinyl, thiazolyl, isothiazolyl, oxazolyl, isoxazolyl, furazanyl, pyrrolidinyl, 2-pyrrolinyl, imidazolidinyl, 2-imidazolinyl, pyrazolidinyl, 3-pyrazolinyl, piperidinyl piperazinyl, morpholinyl, pyranyl, tetrahydropyranyl, tetrazoyl, dioxanyl, dioxolanyl, benzofuryl, isobenzofuryl, chromenyl, indolizinyl, isoindolyl, indolyl, indazolyl, purinyl, quinolyl, phthalazinyl, quinazolinyl, pteridinyl, isochromanyl, indolinyl and isoindolinyl groups, optionally substituted by one or more groups chosen from hydroxyl, mercapto, straight-chain or branched C$_1$-C$_6$ alkyl, straight-chain or branched C$_1$-C$_6$ hydroxyalkyl, straight-chain or branched C$_1$-C$_6$ polyhydroxyalkyl, straight-chain or branched C$_1$-C$_6$ alkoxy-C$_1$-C$_6$ alkyl, straight-chain or branched C$_1$-C$_6$ hydroxyalkoxy-C$_1$-C$_6$ alkyl and straight-chain or branched C$_1$-C$_6$ polyhydroxyalkoxy-C$_1$-C$_6$ alkyl groups, with the proviso that when p and q are equal to 0, the groups in R$_6$ and R$_7$ attached directly to

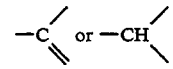

are selected from —CH$_2$—,

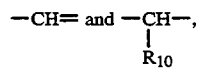

R$_{10}$ being as defined above;
or W representing a group

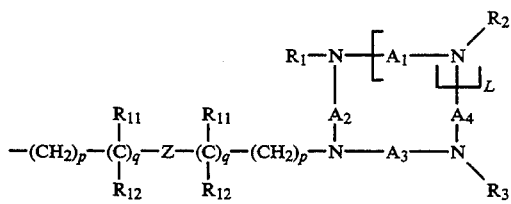

in which p, q, $R_1$, $R_2$, $R_3$, $R_{11}$, $R_{12}$, $A_1$, $A_2$, $A_3$ and $A_4$ are as defined above and Z represents a heterocycle, optionally formed from two fused rings, containing up to 12 members, 1 to 4 of which are heteroatoms chosen from oxygen, —N=,

$R_8$ being as defined above, phosphorus and sulphur, the heterocycle being optionally substituted by one or more groups chosen from hydroxyl, mercapto, straight-chain or branched $C_1$-$C_6$ alkyl, straight-chain or branched $C_1$-$C_6$-hydroxyalkyl or -polyhydroxyalkyl, straight-chain or branched $C_1$-$C_6$ alkoxy -$C_1$-$C_6$ alkyl and straight-chain or branched $C_1$-$C_6$-hydroxyalkoxy-or -polyhydroxyalkoxy- $C_1$-$C_6$ alkyl, and a functional group enabling the binding of a macromolecule;

L represents an integer from 0 to 5 where at least two of the groups $R_1$, $R_2$ and $R_3$ represent

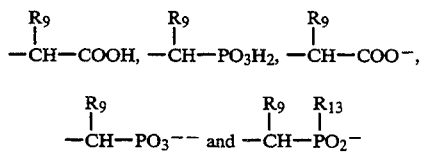

$R_9$ and $R_{13}$ being as defined above; it being understood that the groups $A_1$, $R_2$, $R_4$, $R_5$, $R_8$, $R_9$, $R_{10}$, $R_{11}$, $R_{12}$ and $R_{13}$ may differ from $A_1$, $R_2$, $R_4$, $R_5$, $R_8$, $R_9$, $R_{10}$, $R_{11}$, $R_{12}$ and $R_{13}$ respectively when L, m, n and q are other than 0, or when several of said groups are present, as well as the salts of these compounds formed with inorganic or organic bases, or basic amino acids.

2. Ligands according to claim 1, of formula   I

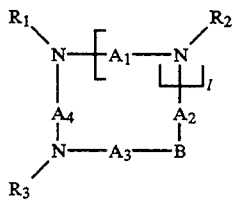

in which $A_1$, $A_2$, $A_3$ and $A_4$, which may be identical or different, independently of one another represent a group:

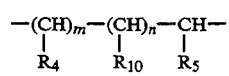

m and n being identical or different integers such that the sum of m and n is between 1 and 5, $R_4$ and $R_5$, which may be identical or different, represent a hydrogen atom, a straight-chain or branched $C_1$-$C_6$ alkyl group, a straight-chain or branched $C_1$-$C_6$ hydroxyalkyl or polyhydroxyalkyl group, a functional group enabling the macrocycle of formula I to be attached to a macromolecule, a straight-chain or branched $C_1$-$C_6$ alkoxy -$C_1$-$C_6$ alkyl group, a straight-chain or branched hydroxy -$C_1$-$C_6$ alkoxy -$C_1$-$C_6$ alkyl group or a straight-chain or branched $C_1$-$C_6$ polyhydroxyalkoxy -$C_1$-$C_6$ alkyl group, an aryl group or an aryl group substituted by one or more identical or different substituents chosen from a halogen atom, a hydroxyl group, a nitro group or a $C_1$-$C_6$ alkyl, $C_1$-$C_6$ hydroxyalkyl, $C_1$-$C_6$ polyhydroxyalkyl, $C_1$-$C_6$ alkoxy or $C_1$-$C_6$ alkoxy-$C_1$-$C_6$ alkyl group, an aralkyl group or an aralkyl group substituted by one or more identical or different substituents chosen from a halogen atom, a hydroxyl group, a nitro group or a $C_1$-$C_6$ alkyl, $C_1$-$C_6$ hydroxyalkyl, $C_1$-$C_6$ polyhydroxyalkyl, $C_1$-$C_6$ alkoxy or $C_1$-$C_6$ alkoxy-$C_1$-$C_6$ alkyl group, the alkyl radical of the aralkyl group being $C_1$-$C_6$ and straight-chain or branched, $R_{10}$ represents the group $R_4$ or $R_5$, a hydroxyl group or a $C_1$-$C_6$ alkoxy group, $R_1$, $R_2$ and $R_3$, which may be identical or different, are chosen from a hydrogen atom and the

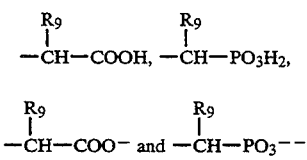

groups, $R_9$ representing a hydrogen atom, a straight-chain or branched $C_1$-$C_6$ alkyl group, a straight-chain or branched $C_1$-$C_6$ hydroxyalkyl group, a straight-chain or branched $C_1$-$C_6$ polyhydroxyalkyl group or a straight-chain or branched $C_1$-$C_6$ alkoxyl -$C_1$-$C_6$ alkyl group, B represents the group

W representing the group

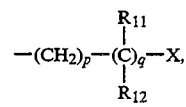

in which p and q are identical or different integers from 0 to 6, $R_{11}$ and $R_{12}$, which may be identical or different, have the same meaning as $R_{10}$ when p is other than 0 and have the same meaning as $R_4$ and $R_5$ when p is equal to 0 and X represents a group

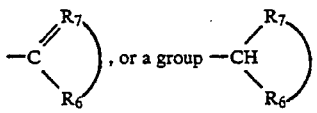

$R_6$ and $R_7$ forming, with the carbon atom to which they are attached, a heterocycle, containing up to 12 members, selected from thienyl, dihydrothienyl, tetrahydrothienyl, furyl, dihydrofuryl, tetrahydrofuryl, pyranyl, dihydropyranyl, tetrahydropyranyl, pyrrolyl, 2H-pyrrolyl, dihydropyrrolyl, tetrahydropyrrolyl, imidazolyl, pyrazolyl, pyridyl, pyrazinyl, pyrimidinyl, pyridazinyl, thiazolyl, isothiazolyl, oxazolyl, isoxazolyl, furazanyl, pyrrolidinyl, 2-pyrrolinyl, imidazolidinyl, 2-imidazolinyl, pyrazolidinyl, 3-pyrazolinyl, piperidinyl piperazinyl, morpholinyl, pyranyl, tetrahydropyranyl, tetrazoyl, dioxanyl, dioxolanyl, benzofuryl, isobenzofuryl, chromenyl, indolizinyl, isoindolyl, indolyl, indazolyl, purinyl, quinolyl, phthalazinyl, quinazolinyl, pteridinyl, isochromanyl, indolinyl and isoindolinyl groups, optionally substituted by one or more groups chosen from hydroxyl, mercapto, straight-chain or branched $C_1$-$C_6$ alkyl, straight-chain or branched $C_1$-$C_6$ hydroxyalkyl, straight-chain or branched $C_1$-$C_6$ polyhydroxyalkyl, straight-chain or branched $C_1$-$C_6$-alkoxy -$C_1$-$C_6$ alkyl, straight-chain or branched $C_1$-$C_6$-hydroxyalkoxy-$C_1$-$C_6$ alkyl and straight-chain or branched $C_1$-$C_6$ polyhydroxyalkoxy-$C_1$-$C_6$ alkyl groups, on condition that when p and q are equal to 0, the groups in $R_6$ and $R_7$ attached directly to

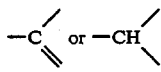

are selected from —CH$_2$—, —CH= and

$R_{10}$ being as defined above;

L represents an integer from 0 to 5; with the proviso that at least two of the groups among $R_1$, $R_2$ and $R_3$ represent

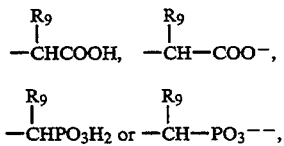

$R_9$ being as defined above; it being understood that the groups $A_1$, $R_2$, $R_4$, $R_5$, $R_8$, $R_9$, $R_{10}$, $R_{11}$ and $R_{12}$ may differ from $A_1$, $R_2$, $R_4$, $R_5$, $R_8$, $R_9$, $R_{10}$, $R_{11}$ and $R_{12}$ respectively when L, m, n and q are other than 0, or when several of said groups are present, as well as the salts of these compounds formed with inorganic or organic bases, or basic amino acids.

3. Ligands according to claim 2, in which X is chosen from pyrrolidinyl, imidazolyl, oxazolyl, pyrrolyl, pyridyl, pyranyl, tetrahydropyranyl, furyl, dihydrofuryl, tetrahydrofuryl, dioxanyl, oxazinyl, thienyl, morpholinyl, piperidinyl and dioxolanyl, in which groups the nitrogen atom is optionally substituted by a $C_1$-$C_6$ alkyl group, a straight-chain or branched $C_1$-$C_6$ hydroxyalkyl group, a straight-chain or branched $C_1$-$C_6$ polyhydroxyalkyl group or a straight-chain or branched $C_1$-$C_6$ alkoxy group, the carbon atoms of the heterocycle optionally carrying one or more substituents chosen from hydroxyl, mercapto, $C_1$-$C_6$ alkyl and $C_1$-$C_6$ hydroxyalkyl.

4. Ligands of general formula I according to claim 1, in which Z is chosen from the following groups: thiophenediyl, dihydrothiophenediyl, tetrahydrothiophenediyl, furandiyl, dihydrofurandiyl, tetrahydrofurandiyl, pyrandiyl, dihydropyrandiyl, tetrahydropyrandiyl, pyrrolediyl, 2H-pyrrolediyl, dihydropyrrolediyl, tetrahydropyrrolediyl, imidazolediyl, pyrazolediyl, pyridinediyl, 3-hydroxy-6-methyl-2-pyridinediyl, pyrazinediyl, pyrimidinediyl, pyridazinediyl, thiazolediyl, isothiazolediyl, oxazolediyl, isoxazolediyl, furazandiyl, pyrrolidinediyl, Δ2-pyrrolinediyl, imidazolinediyl, Δ2-imidazolinediyl, pyrazolidinediyl, Δ3-pyrazolinediyl, piperidinediyl, piperazinediyl, morpholinediyl, pyrandiyl, tetrahydropyrandiyl, tetrazolediyl, dioxanediyl, dioxolanediyl, benzofurandiyl, isobenzofurandiyl, chromenediyl, indolizinediyl, purinediyl, quinolinediyl, phthalazinediyl, quinazolinediyl, pteridinediyl, isochromandiyl, indolediyl, isoindolediyl, indazolediyl, indolinediyl and isoindolinediyl, optionally substituted by one or more groups chosen from hydroxyl, mercapto, straight-chain or branched $C_1$-$C_6$ alkyl, straight-chain or branched $C_1$-$C_6$ hydroxyalkyl, straight-chain or branched $C_1$-$C_6$ polyhydroxyalkyl, straight-chain or branched $C_1$-$C_6$ alkoxy, straight-chain or branched $C_1$-$C_6$ alkoxy-$C_1$-$C_6$ alkyl, straight-chain or branched $C_1$-$C_6$ hydroxyalkoxy-$C_1$-$C_6$-alkyl and straight-chain or branched $C_1$-$C_6$ polyhydroxyalkoxy-$C_1$-$C_6$-alkyl.

5. Ligands according to claim 1, in which the functional group enabling binding of a macromolecule is chosen from the groups of formula:

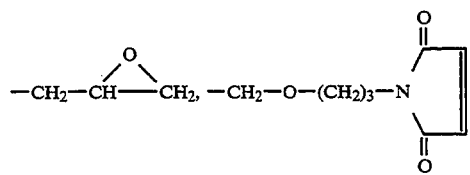

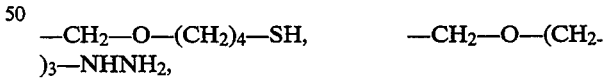

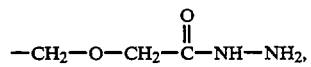

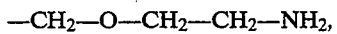

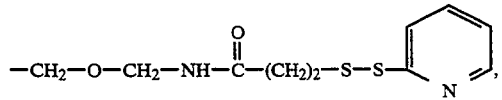

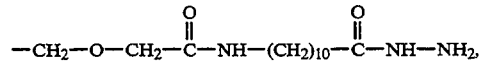

-continued

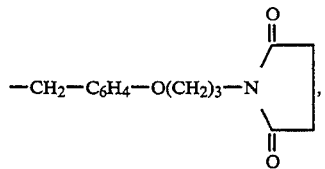

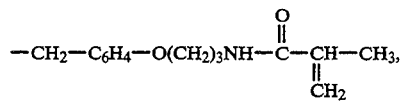

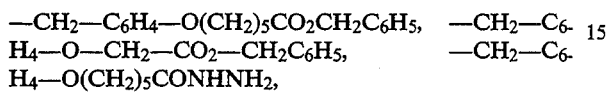

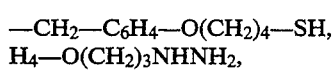, 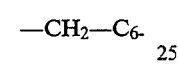

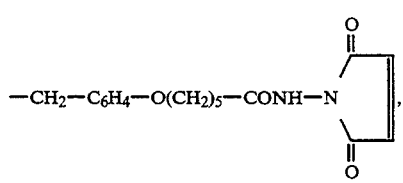

—CH$_2$—C$_6$H$_4$—O(CH$_2$)$_3$Br, —CH$_2$—C$_6$H$_4$—O(CH$_2$)$_5$CONHNH—(CH$_2$)$_3$—NHNH$_2$, —CH$_2$—SH, —CH$_2$—NHNH$_2$, —CH$_2$CONHNH$_2$, (CH$_2$)$_3$SH, —CH$_2$—C$_6$H$_4$—O—CH$_2$—COBr, —C$_6$H$_4$NHCOCH$_2$Br, —CH$_2$—C$_6$H$_4$—OCH$_2$—C—NH—(CH$_2$)$_2$NH$_2$, —CH$_2$—C$_6$H$_4$—NH$_2$, —C$_6$H$_4$—N$_2$, —C$_6$H$_4$NCS,

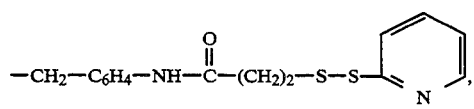

—NHCO—NH—NH$_2$, —NCS—NH—NH$_2$,

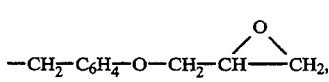

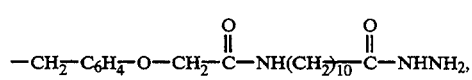

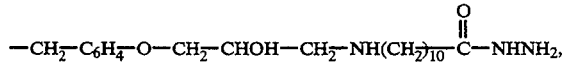

and

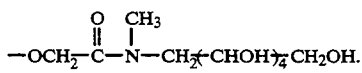

6. Ligands according to claim 1, in which w is chosen from the groups:

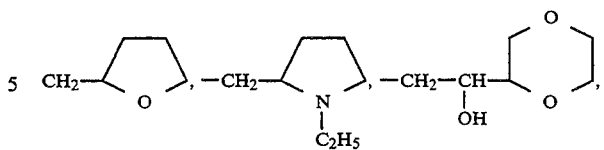

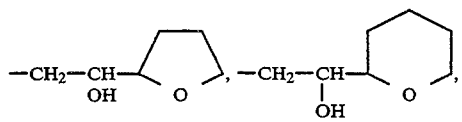

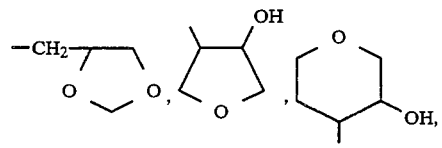

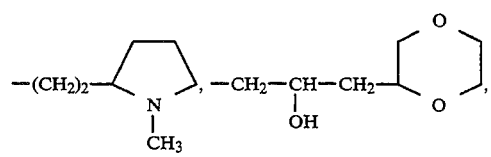

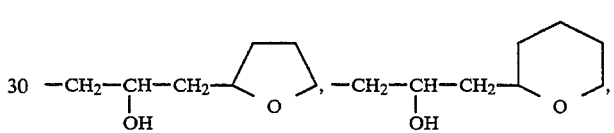

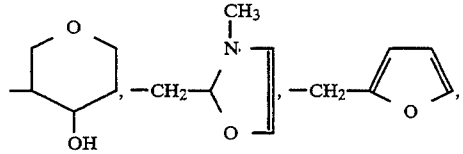

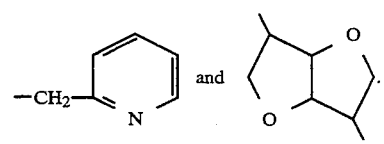

7. Ligands of formula:

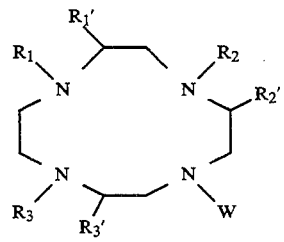

in which R$_1$, R$_2$, R$_3$ and W have the same meaning as in formula I according to claim 1 and R′$_1$, R′$_2$ and R′$_3$, which may be identical or different, represent a hydrogen atom, a straight-chain or branched C$_1$-C$_6$ alkyl group, a straight-chain or branched C$_1$-C$_6$ hydroxyalkyl or polyhydroxyalkyl group, a functional group enabling the macrocycle of formula I to be attached to a macromolecule, a straight-chain or branched C$_1$-C$_6$ alkoxy-C$_1$-C$_6$ alkyl group, a straight-chain or branched hydroxy-C$_1$-C$_6$alkoxy-C$_1$-C$_6$-alkyl group or a straight-chain or branched polyhydroxy-$C_1$-$C_6$alkoxy-$C_1$-$C_6$alkyl group, an aryl group or an aryl group substituted by one or more identical or different substituents chosen from a halogen atom, a hydroxyl group, a nitro group or a $C_1$-$C_6$ alkyl, $C_1$-$C_6$ hydroxyalkyl, $C_1$-$C_6$ polyhydroxyalkyl, $C_1$-$C_6$ alkoxy or $C_1$-$C_6$alkoxy-$C_1$-$C_6$ alkyl group, an aralkyl group or an aralkyl group substituted by one or more identical or different substituents chosen from a halogen atom, a hydroxyl group, a nitro group or a $C_1$-$C_6$ alkyl, $C_1$-$C_6$ hydroxyalkyl, $C_1$-$C_6$ polyhydroxyalkyl, $C_1$-$C_6$ alkoxy or $C_1$-$C_6$ alkoxy-$C_1$-$C_6$ alkyl group, the alkyl radical of the aralkyl group being $C_1$-$C_6$ and straight-chain or branched, with the proviso that at least two groups among $R_1$, $R_2$ or $R_3$ represent

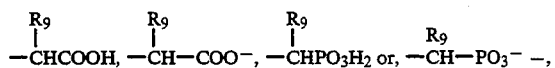

where $R_9$ is as defined in claim 1, as well as the salts of these ligands obtained with organic or inorganic bases or basic amino acids.

8. Ligands chosen from the compounds of formula III

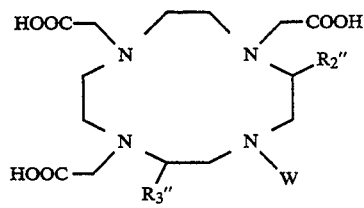

III in which $R''_2$ and $R''_3$ are chosen from a hydrogen atom, a methyl group and an ethyl group and W is as defined in claim 4.

9. Ligand chosen from the compounds of formula III according to claim 8, in which $R''_2$ and $R''_3$ represent a hydrogen atom and W is selected from the groups:

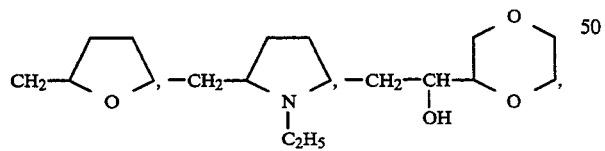

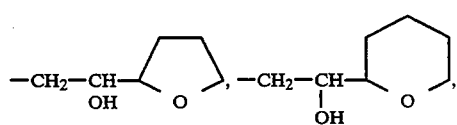

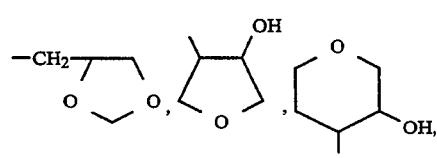

-continued

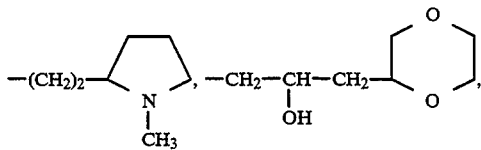

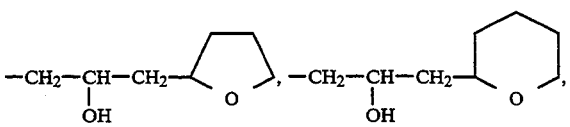

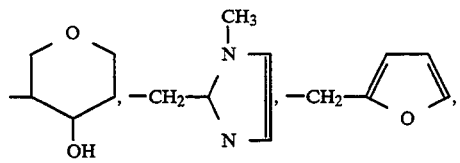

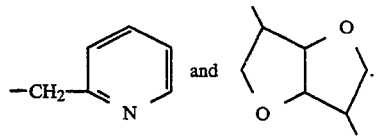

10. Ligand of formula

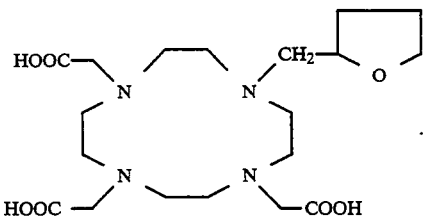

11. Ligand of formula III according to claim 8, in which $R''_2$ and $R''_3$ represent a methyl group and W represents

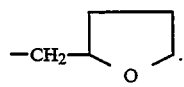

12. Ligand of formula

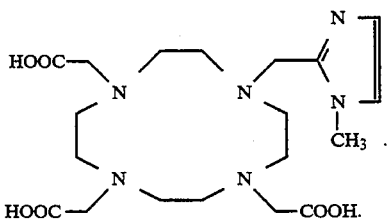

13. Ligand of formula

14. Ligand of formula:

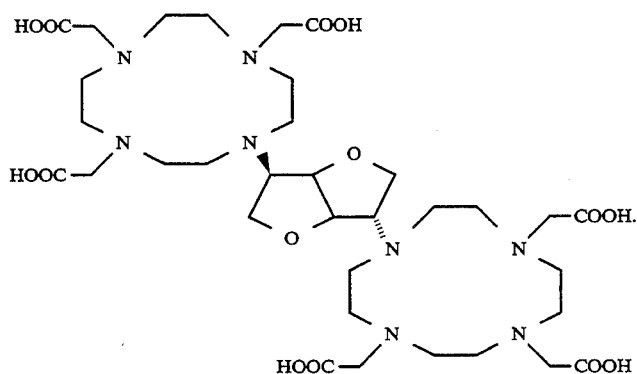

15. Ligand of formula

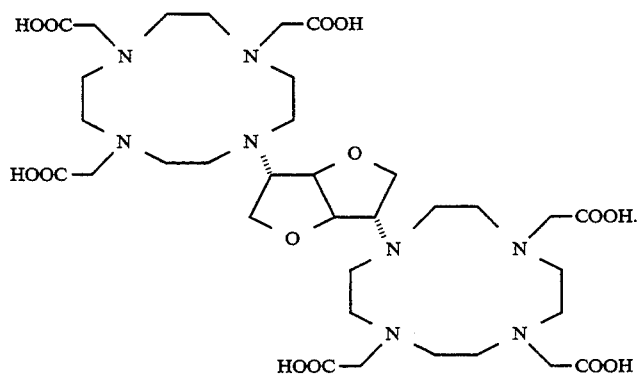

16. Neutral or ionic monometallic or polymetallic complexes formed by at least one ligand of formula I according to claim 1 with at least one metal ion chosen from lanthanide ions, transition metal ions, barium, bismuth, lead and the radioisotopes $^{99m}Tc$, $^{111}In$, $^{90}Y$, $^{64}Cu$ and $^{169}Yb$, as well as the salts of these complexes with pharmaceutically acceptable inorganic or organic bases or basic amino acids.

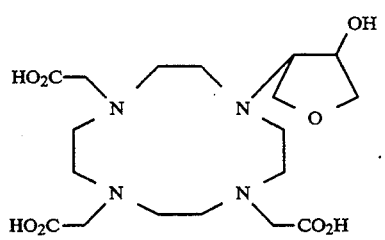

17. Monometallic or bimetallic complexes according to claim 16, in which the metal ion is chosen from gadolinium, europium, dysprosium, iron ($Fe^{3+}$), manganese ($Mn^{2+}$) and barium.

18. Diagnostic composition, characterised in that it contains at least one complex according to either of claim 16.

19. Composition according to claim 18, consisting of a solution of the complex in an aqueous solvent.

* * * * *